(12) United States Patent
Edge et al.

(10) Patent No.: US 12,419,876 B2
(45) Date of Patent: *Sep. 23, 2025

(54) TREATMENT OF HEARING LOSS BY INHIBITION OF CASEIN KINASE 1

(71) Applicant: Massachusetts Eye and Ear Infirmary, Boston, MA (US)

(72) Inventors: Albert Edge, Brookline, MA (US); Yenfu Cheng, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 894 days.

This patent is subject to a terminal disclaimer.

(21) Appl. No.: 17/450,377

(22) Filed: Oct. 8, 2021

(65) Prior Publication Data

US 2022/0016100 A1    Jan. 20, 2022

Related U.S. Application Data

(62) Division of application No. 15/781,041, filed as application No. PCT/US2016/064727 on Dec. 2, 2016, now Pat. No. 11,185,536.

(60) Provisional application No. 62/263,412, filed on Dec. 4, 2015.

(51) Int. Cl.
| | |
|---|---|
| A61K 31/437 | (2006.01) |
| A61K 9/00 | (2006.01) |
| A61K 31/4439 | (2006.01) |
| A61K 38/00 | (2006.01) |
| A61P 27/16 | (2006.01) |
| C07D 401/04 | (2006.01) |
| C07D 403/04 | (2006.01) |
| C07D 405/14 | (2006.01) |
| C07D 413/14 | (2006.01) |
| C07D 487/04 | (2006.01) |
| C12Q 1/48 | (2006.01) |

(52) U.S. Cl.
CPC ........ *A61K 31/4439* (2013.01); *A61K 9/0046* (2013.01); *A61K 31/437* (2013.01); *A61K 38/00* (2013.01); *A61P 27/16* (2018.01); *C07D 401/04* (2013.01); *C07D 403/04* (2013.01); *C07D 405/14* (2013.01); *C07D 413/14* (2013.01); *C07D 487/04* (2013.01); *C12Q 1/485* (2013.01); *G01N 2800/14* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| D309,535 S | 7/1990 | Wilson |
| D360,535 S | 7/1995 | Sjoberg |
| 5,695,995 A | 12/1997 | Weintraub et al. |
| D447,031 S | 8/2001 | Oh |
| 6,417,185 B1 | 7/2002 | Goff et al. |
| 6,489,344 B1 | 12/2002 | Nuss et al. |
| 6,608,063 B2 | 8/2003 | Nuss et al. |
| 6,756,511 B2 | 6/2004 | Castro Pineiro et al. |
| 6,890,956 B2 | 5/2005 | Churcher et al. |
| 6,984,626 B2 | 1/2006 | Nadin et al. |
| 7,049,296 B2 | 5/2006 | Castro Pineiro et al. |
| 7,101,895 B2 | 9/2006 | Churcher et al. |
| 7,138,400 B2 | 11/2006 | Collins et al. |
| 7,144,910 B2 | 12/2006 | Madin et al. |
| 7,183,303 B2 | 2/2007 | Castro Pineiro et al. |
| 7,206,639 B2 | 4/2007 | Jacobsen et al. |
| 7,399,633 B2 | 7/2008 | Bernstein et al. |
| D646,625 S | 10/2011 | Youn |
| 8,188,069 B2 | 5/2012 | Miller et al. |
| 8,518,944 B2 | 8/2013 | Subramanyam et al. |
| 8,617,810 B2 | 12/2013 | Heller et al. |
| 8,673,634 B2 | 3/2014 | Li et al. |
| 10,406,163 B2 | 9/2019 | Edge et al. |
| 10,603,295 B2 | 3/2020 | Edge et al. |
| 10,925,872 B2 | 2/2021 | Lorrain et al. |
| 2003/0114381 A1 | 6/2003 | Cotanche et al. |
| 2004/0029862 A1 | 2/2004 | Belanger et al. |
| 2004/0049038 A1 | 3/2004 | Collins et al. |
| 2004/0186147 A1 | 9/2004 | Hannam et al. |
| 2005/0019801 A1 | 1/2005 | Rubin et al. |
| 2005/0119293 A1 | 6/2005 | Collins et al. |
| 2005/0143369 A1 | 6/2005 | Castro Pineiro et al. |
| 2005/0182109 A1 | 8/2005 | Collins et al. |
| 2005/0182111 A1 | 8/2005 | Pineiro et al. |
| 2005/0215602 A1 | 9/2005 | Campbell et al. |

(Continued)

FOREIGN PATENT DOCUMENTS

| | | |
|---|---|---|
| CN | 1441841 | 9/2003 |
| GB | 2459910 | 11/2009 |

(Continued)

OTHER PUBLICATIONS

Schittek et al (Molecular Cancer 13:231 (14 pages), 2014) (Year: 2014).*
Office Action in Japanese Appln. No. 2022-069599, dated Jun. 6, 2023, 3 pages (with English translation).
Arnold et al., "Sox2+adult stem and progenitor cells are important for tissue regeneration and survival of mice," Cell Stem Cell, Oct. 2011, 9(4):317-29.
Cohen-Salmon et al., "Targeted ablation of connexin26 in the inner ear epithelial gap junction network causes hearing impairment and cell death," Curr Biol., Jul. 2002, 12(13):1106-11.

(Continued)

*Primary Examiner* — Craig D Ricci
(74) *Attorney, Agent, or Firm* — Fish & Richardson P.C.

(57) ABSTRACT

Methods for treating hearing loss that include administering an inhibitor, e.g., a small molecule inhibitor, of casein kinase 1, preferably in combination with a treatment that stimulates Atoh1 gene expression, e.g., a gamma-secretase inhibitor, an Atoh1 stimulatory compound, or a GSK-3-beta inhibitor.

14 Claims, 8 Drawing Sheets

Specification includes a Sequence Listing.

(56) References Cited

U.S. PATENT DOCUMENTS

| | | |
|---|---|---|
| 2005/0287127 A1 | 12/2005 | Li et al. |
| 2006/0030837 A1 | 2/2006 | McKenna et al. |
| 2007/0093878 A1 | 4/2007 | Edge et al. |
| 2008/0146617 A1 | 6/2008 | Aud et al. |
| 2008/0267929 A1 | 10/2008 | Li et al. |
| 2009/0098093 A1 | 4/2009 | Edge |
| 2009/0099237 A1 | 4/2009 | Aud et al. |
| 2009/0124568 A1 | 5/2009 | Heller et al. |
| 2009/0232780 A1 | 9/2009 | Edge et al. |
| 2009/0297533 A1 | 12/2009 | Lichter et al. |
| 2009/0306225 A1 | 12/2009 | Lichter et al. |
| 2010/0273864 A1 | 10/2010 | Lichter et al. |
| 2011/0020232 A1 | 1/2011 | Eberhart et al. |
| 2011/0033480 A1 | 2/2011 | Sarkar et al. |
| 2011/0305674 A1* | 12/2011 | Edge .................. A61K 45/06 514/21.2 |
| 2011/0319377 A1 | 12/2011 | Lichter et al. |
| 2013/0085112 A1 | 4/2013 | Collard et al. |
| 2013/0210145 A1 | 8/2013 | Edge |
| 2013/0225543 A1 | 8/2013 | Jones et al. |
| 2014/0044763 A1 | 2/2014 | Kustov et al. |
| 2015/0030568 A1 | 1/2015 | Li et al. |
| 2015/0209406 A1 | 7/2015 | Chen |
| 2017/0349884 A1 | 12/2017 | Karp et al. |
| 2018/0148456 A1 | 5/2018 | Clay et al. |
| 2019/0010449 A1 | 1/2019 | Edge et al. |
| 2019/0203210 A1 | 7/2019 | Edge et al. |
| 2019/0247381 A1 | 8/2019 | Edge et al. |
| 2020/0255800 A1 | 8/2020 | Edge |
| 2021/0290686 A1 | 9/2021 | Edge et al. |
| 2021/0299138 A1 | 9/2021 | Edge et al. |
| 2022/0008433 A1 | 1/2022 | Edge et al. |
| 2022/0259602 A1 | 8/2022 | Edge et al. |

FOREIGN PATENT DOCUMENTS

| | | |
|---|---|---|
| JP | 2006-117536 | 5/2006 |
| JP | 2006/520386 | 9/2006 |
| JP | 2007/503816 | 3/2007 |
| JP | 2007/526248 | 9/2007 |
| JP | 2011-518195 | 6/2011 |
| JP | 2012-509899 | 4/2012 |
| WO | WO 1998/028268 | 7/1998 |
| WO | WO 2000/053632 | 9/2000 |
| WO | WO 2000/059939 | 10/2000 |
| WO | WO 2001/070677 | 9/2001 |
| WO | WO 2002/049038 | 6/2002 |
| WO | WO 2003/093251 | 11/2003 |
| WO | WO 2003/093252 | 11/2003 |
| WO | WO 2003/093253 | 11/2003 |
| WO | WO 2003/093264 | 11/2003 |
| WO | WO 2004/039370 | 5/2004 |
| WO | WO 2004/039800 | 5/2004 |
| WO | WO 2005/014553 | 2/2005 |
| WO | WO 2005/030731 | 4/2005 |
| WO | WO 2006/026570 | 3/2006 |
| WO | WO 2007/075911 | 7/2007 |
| WO | WO 2008/076556 | 6/2008 |
| WO | WO 2009/087130 | 7/2009 |
| WO | WO 2009/132050 | 10/2009 |
| WO | WO 2010/060088 | 5/2010 |
| WO | WO 2012/005805 | 1/2012 |
| WO | WO 2014/145205 | 9/2014 |
| WO | WO 2014/159356 | 10/2014 |
| WO | WO 2015/168149 | 11/2015 |
| WO | WO 2016/022776 | 2/2016 |
| WO | WO 2016/037016 | 3/2016 |
| WO | WO 2017/151907 | 9/2017 |
| WO | WO 2018/111926 | 6/2018 |

OTHER PUBLICATIONS

Elgoyhen and Franchini, "Prestin and the cholinergic receptor of hair cells: positively-selected proteins in mammals," HHS Public Access Author Manuscript, doi: 10.1016/j.heares.2009.12.028, published online Jan. 6, 2010, published in final edited form as: Hear Res, Mar. 2011, 273(1-2):100-8, 19 pages.

Fritzsch et al., "The molecular basis of neurosensory cell formation in ear development: a blueprint for hair cell and sensory neuron regeneration?," Bioessays, Dec. 2006, 28(12):1181-93, 13 pages.

Fujioka et al., "Generating mouse models of degenerative diseases using cre/lox-mediated in vivo mosaic cell ablation," J Clin Invest, Jun. 2011, 121(6):2462-9.

Harding et al., "The effect of an age-related hearing loss gene (Ahl) on noise-induced hearing loss and cochlear damage from low-frequency noise," Hear Res, Jun. 2005, 204(1-2):90-100, 5 pages (Abstract only).

Hudspeth, "Making an effort to listen: mechanical amplification in the ear," Neuron, Aug. 2008, 59(4):530-45.

Kujawa and Liberman, "Conditioning-related protection from 15 acoustic injury: effects of chronic deefferentation and sham surgery," J Neurophysiol, Dec. 1997, 78(6):3095-106.

Löwenheim et al., "Gene disruption of p27Kip1 allows cell 15 proliferation in the postnatal and adult organ of corti," Proc Natl Acad Sci U S A, Mar. 1999, 96(7):4084-8.

Maison et al., "Loss of αCGRP reduces sound-evoked activity in the cochlear nerve," J Neurophysiol, Nov. 2003, 90(5):2941-9.

Mantela et al., "The retinoblastoma gene pathway regulates the postmitotic state of hair cells of the mouse inner ear," Development, May 2005, 132(10):2377-2388.

Martinez-Monedero et al., "Differentiation of inner ear stem cells to functional sensory neurons," Dev Neurobiol., Apr. 2008, 68(5):669-684.

Muzumdar et al., "A global double-fluorescent Cre reporter mouse," Genesis, Sep. 2007, 45(9):593-605.

Nayak et al., "Development of the hair bundle and mechanotransduction," Int J Dev Biol., 2007, 51(6-7):597-608.

Richardson et al., "How the genetics of deafness illuminates auditory physiology," Annu Rev Physiol., 2011, 73:311-34.

Sage et al., "Essential role of retinoblastoma protein in mammalian hair cell development and hearing," Proc Natl Acad Sci U S A, May 2006, 103(19):7345-50.

Sage et al., "Proliferation of functional hair cells in vivo in the absence of the retinoblastoma protein," Science, Feb. 2005, 307(5712):1114-8.

Warchol, "Sensory regeneration in the vertebrate inner ear: Differences at the levels of cells and species," Hear Res, Mar. 2011, 273(1-2):72-9, 5 pages (Abstract only).

Costa et al., "Atoh1 in sensory hair cell development: constraints and cofactors," Seminars in Cell & Developmental Biology, May 2017, 65:60-68.

Office Action in Korean Appln. No. 10-2018-7024892, dated Sep. 19, 2024, 30 pages (with English translation).

Romand et al., "The retinoic acid receptors RARα and RARγ are required for inner ear development," Mechanisms of Development, Dec. 2002, 119(2):213-223.

Pickering et al., "The implications of structured 5' untranslated regions on translation and disease," Semin Cell Dev Biol., Feb. 2005, 16(1):39-47.

TakaraBio.com [online], "MSCV retrovirus system," 2025, retrieved on Mar. 14, 2025, retrieved from URL<https://www.takarabio.com/products/gene-function/viral-transduction/retrovirus/vector-systems/mscv-system>, 2 pages.

Abbott et al., "Coordinated regulation of Toll-like receptor and NOD2 signaling by K63-linked polyubiquitin chains," Molecular and Cellular Biology, 2007, 27:6012-6025.

Adam et al., "Cell fate choices and the expression of Notch, Delta and Serrate homologues in the chick inner ear: parallels with *Drosophila* sense-organ development," Development, 125(23):4645-54 (Dec. 1998).

Adamo et al., "LSD1 regulates the balance between self-renewal and differentiation in human embryonic stem cells," Nat Cell Biol, Jun. 2011, 13(6):652-659, 20 pages.

Adhikary et al., The ubiquitin ligase HectH9 regulates transcriptional activation by Myc and is essential for tumor cell proliferation, Cell, 2005, 123 :409-421.

(56) References Cited

OTHER PUBLICATIONS

Adler and Raphael, "New hair cells arise from supporting cell conversion in the acoustically damaged chick inner ear," Neuroscience Letters, Feb. 1996, 205: 17-20.
Ahmed and Streit, "LSD1 interacts with cMyb to demethylate repressive histone marks and maintain inner ear progenitor identity," Development, 2018, 145(4):dev160325, 9 pages.
Aletsee et al., "The disintegrin Kistrin inhibits neurite extension from spiral ganglion explants cultured on laminin," Audiol. Neurootol., 6:57-65 (2001).
Armstrong et al, "Porcine neural xenografts in the immunocompetent rat: immune response following grafting of expanded neural precursor cells," Neuroscience, Sep. 2001, 106(1):201-216.
Artavanis-Tsakonas et al., "Notch Signaling," Sci., 1995, 268:225-232.
Azuara et al., "Chromatin signatures of pluripotent cell lines," Nat Cell Biol, May 2006, 8(5):532-538, 11 pages.
Ballas et al., "Regulation of neuronal traits by a novel transcriptional complex," Neuron, Aug. 2001, 31(3):353-365.
Barker et al., "A Role for Complement in the Rejection of Porcine Ventral Mesencephalic Xenografts in a Rat Model of Parkinson's Disease," The Journal of Neuroscience, May 2000, 20(9):3415-3424.
Barker et al., "Identification of stem cells in small intestine and colon by marker gene Lgf5," Nature, 2007, 449: 1003-1007.
Barker, "Wnt Signaling: vol. 1: Pathway Methods and Mammalian Models," in Methods in Molecular Biology, Nov. 2008, 5-15.
Bartolami et al., "Appearance and Distribution of the 275 kD Hair-Cell Antigen During Development of the Avian Inner Ear," J. Comp. Neurol., 314:777-788 (1991).
Basi et al., "Amyloid precursor protein selective gamma-secretase inhibitors for treatment Amyloid precursor protein selective gamma-secretase of Alzheimer's disease," Alzheimer's Research & Therapy, 2:36 (2010) pp. 1-21.
Batts et al., "Notch signaling and Hes labeling in the normal and drug-damaged organ of Corti," Hear Res., 249:15-22 (Mar. 2009).
Becvarovski et al., "Round Window Gentamicin Absorption: An In Vivo Human Model," Laryngoscope, Sep. 2002, 112: 1610-1613.
Ben-Arie et al., "Math1 is essential for genesis of cerebellar granule neurons." Nature, 1997, 390: 169-172.
Ben-Arie et al., "Functional conservation of atonal and Math1 in the CNS and PNS," Development, 2000, 127:1039-1048.
Bermingham et al., "Math1: An Essential Gene for the Generation of Inner Ear Hair Cells," Science, 1999, 284: 1837-1841.
Bernstein et al., "A bivalent chromatin structure marks key developmental genes in embryonic stem cells," Cell, Apr. 2006, 125(2):315-326.
Bernstein et al., "Methylation of histone H3 Lys 4 in coding regions of active genes," Proc Natl Acad Sci U S A, Jun. 2002, 99(13):8695-8700.
Bertrand et al., "Proneural genes and the specification of neural cell types," Nature Reviews Neuroscience, 2002, 3:517-530.
Beurel et al., "Glycogen synthase kinase-3 (GSIG): Regulation, actions, and diseases," Pharmacology & Therapeutics, 2015, 148:114-131.
Bodson et al., "Hair cell progenitors: identification and regulatory genes," Acta Otolaryngol, Mar. 2010, 130(3):312-7.
Borden et al., "Hyaluronic Acid Hydrogel Sustains the Delivery of Dexamethasone across the Round Window Membrane," Audiol Neurootol., 2011, 16(1):1-11.
Bossuyt et al., "Atonal homolog 1 is a tumor suppressor gene," PLoS Biology, 2009, 7:e39.
Bouchard et al., "Pax2 and homeodomain proteins cooperatively regulate a 435 bp enhancer of the mouse Pax5 gene at the midbrain-hindbrain boundary," Develop., 127:1017-28 (2000).
Bramhall, "Lgr5-Positive Supporting Cells Generate New Hair Cells in the Postnatal Cochlea," Stem Cell Reports, Mar. 2014, 2:1-12.
Breuskin et al., "Strategies to regenerate hair cells: identification of progenitors and critical genes," Hear Res, 2008, 236(1-2):1-10.

Brooker et al., "Notch ligands with contrasting functions: Jaggedl and Deltal in the mouse inner ear," Development, 2006, 133:1277-1286.
Brors et al., "EphA4 Provides Repulsive Signals to Developing Cochlear Ganglion Neurites Mediated through Ephrin-B2 and-B3," J. Comp. Neurol., 462:90-100 (2003).
Bryant et al., "Sensory organ development in the inner ear: Molecular and cellular mechanisms," British Medical Bulletin, 63:39-57 (2002).
Burns and Stone, "Development and regeneration of vestibular hair cells in mammals," Semin Cell Dev Biol, 2017, 65: 96-105.
Burns et al., "MYC Gene Delivery to Adult Mouse Utricles Stimulates Proliferation of Postmitotic Supporting Cells In Vitro," PLOS ONE, Oct. 2012, 7: 248704.
Burton et al., "The role of Pax2 in mouse inner ear development," Dev. Biol., 272:161-175 (2004).
CA Office Action in Canadian Appln. No. 2,883,896, dated Jul. 16, 2019, 4 pages.
Cafaro et al., "Atoh1 expression defines activated progenitors and differentiating hair cells during avian hair cell regeneration," Developmental dynamics, 2007, 236:156-170.
Cai et al., "Characterization of the transcriptome of nascent hair cells and identification of direct targets of the Atoh1 transcription factor," J Neurosci, Apr. 2015, 35(14):5870-5883.
Cai et al., "Conditional deletion of Atoh1 reveals distinct critical periods for survival and function of hair cells in the organ of Corti," The Journal of Neuroscience, 2013, 10110-10122.
Caiazzo et al., "Direct generation of functional dopaminergic neurons from mouse and human fibroblasts," Nature, 476:224-7 (Jul. 2011).
Carlisle et al., "Specific expression of Kcna10, Pxn and Odf2 in the organ of Corti," Gene Expr Patterns, May 2012, 12:172-179.
Cau et al., "Mash1 activates a cascade of bHLH regulators in olfactory neuron progenitors," Develop., 124:1611-1621 (1997).
Chai et al., "Wnt signaling induces proliferation of sensory precursors in the postnatal mouse cochlea," PNAS, 2012, 109: 8167-8172.
Charron et al., "The Morphogen Sonic Hedgehog is an Axonal Chemoattractant that Collaborates with Netrin-1 in Midline Axon Guidance," Cell., 113:11-23 (2003).
Chen and Segil, "p27$Kip1$ links cell proliferation to morphogenesis in the developing organ of Corti," Development, 1999, 126(8):1581-1590.
Chen et al., "Histone Demethylase LSD1 Promotes Adipocyte Differentiation through Repressing Wnt Signaling," Cell Chem Biol, Sep. 2016, 23(10):1228-1240.
Chen et al., "ARF-BPI/Mule is a critical mediator of the ARF tumor suppressor," Cell, 2005. 121: 1071-1083.
Chen et al., "The role of Math1 in inner ear development: Uncoupling the establishment of the sensory primordium from hair cell fate determination," Develop., 129:2495-2505 (2002).
Cheng et al., "Destabilization of Atoh1 by E3 Ubiquitin Ligase Huwel and Casein Kinase Is Essential for Normal Sensory Hair Cell Development," Journal of Biological Chemistry, Sep. 2016, 291(40):21096-21109.
Cheng, "Role Of The Ubiquitin-Proteasome Pathway In The Inner Ear: Identification Of An E3 Ubiquitin Ligase For Atoh1," Thesis for the Degree of Doctor of Philosophy in Health Sciences and Technology, Harvard-Massachusetts Institute of Technology, Aug. 29, 2014, 1-99.
Chim et al., "Deafness associated with the use of Bortezomib in multiple myeloma," Acta Oncologica, Jan. 2008, 47(2):323-324.
Chonko et al., "Atoh1 directs hair cell differentiation and survival in the late embryonic mouse inner ear," Dev Biol, Sep. 2013, 381(2):401-410.
Clevers, "Wnt/beta-catenin signaling in development and disease," Cell, 2006, 127:469-480.
Colter et al., "Rapid expansion of recycling stem cells in cultures of plastic-adherent cells from human bone marrow," Proc. Natl. Acad. Sci. U.S.A , 97:3213-3218 (2000).
Corrales et al., "Engraftment and Differentiation of Embryonic Stem Cell-Derived Neural Progenitor Cells in the Cochlear Nerve Trunk: Growth of Processes into the Organ of Corti," J. Neurobiol., 66:1489-500 (2006).

(56) References Cited

OTHER PUBLICATIONS

Corwin et al., "Regeneration of Sensory Hair Cells After Acoustic Trauma," Science, Jun. 1988, 240:1772-1774.
Cosgrove et al., "Integrin alphalbeta1 and transforming growth factor-beta1 play distinct roles in alport glomerular pathogenesis and serve as dual targets for metabolic therapy," Am. J. Pathol., 157:1649-59 (2000).
Cox et al., "Spontaneous hair cell regeneration in the neonatal mouse cochlea in vivo," Development, 2014, 141: 816-829.
Crowder and Freeman, "Glycogen Synthase Kinase-3b Activity Is Critical for Neuronal Death Caused by Inhibiting Phosphatidylinositol 3-Kinase or Akt but Not for Death Caused by Nerve Growth Factor Withdrawal," The Journal of Biological Chemistry, Nov. 2000, 275: 34266-34271.
Dabdoub et al., "Abstract # 443: WNt/B-Catenin Signaling in the Developing Mammalian Cochlea," ARO 31st Annual Midwinter Meeting, Phoenix, Arizona, Feb. 16-21, 2008, 3 pages.
Dabdoub et al., "Abstract # 8: Wnt Signaling in the Developing Mammalian Cochlea, "ARO 30th Annual Midwinter Meeting, Denver, Colorado, Feb. 10-15, 2007, 2 pages.
D'Arca et al., "Huwe 1 ubiquitin ligase is essential to synchronize neuronal and glial differentiation in the developing cerebellum," PNAS, 2010, 107:5875-5880.
Daudet and Lewis, "Two contrasting roles for Notch activity in chick inner ear development: specification of pro sensory patches and lateral inhibition of hair-cell differentiation," Development, 132:541-51 (Feb. 2005).
Daudet et al., "Notch regulation of progenitor cell behavior in quiescent and regenerating auditory epithelium of mature birds," Dev Biol., 326(1):86-100 (Feb. 1, 2009).
Davis, "Hearing disorders in the population: first phase findings of the MRC National Study of Hearing," Hearing Science and Hearing Disorders, 1983, 35-60.
De Groot et al., "Huwel-mediated ubiquitylation of dishevelled defines a negative feedback loop in the Wnt signaling pathway," Science Signaling, Mar. 2014, 7:ra26.
Declaration of Non-Establishment of International Search Report for PCT/US2009/065747, mailed Apr. 8, 2010.
Deshaies and Joazeiro, "RING domain E3 ubiquitin ligases," Annual Review of Biochemistry, 2009, 78:399-434.
Dezawa et al., "Specific induction of neuronal cells from bone marrow stromal cells and application for autologous transplantation," J. Clin. Invest., 113:1701-1710 (2004).
Dobin et al., "STAR: ultrafast universal RNAseq aligner," Bioinformatics, Jan. 2013, 29(1):15-21.
Doetzlhofer et al., "Hey2 regulation by FGF provides a Notch-independent mechanism for maintaining pillar cell fate in the organ of Corti," Dev Cell, 16:58-69 (Jan. 2009).
Dong et al., "Calpain inhibitor MDL28170 modulates Aβ formation by inhibiting the formation of intermediate Aβ46 and protecting Aβ from degradation," The FASEB Journal, Dec. 2005, 21 pages.
D'Onofrio et al., "Advances in the identification of γ-secretase inhibitors for the treatment of Alzheimer's disease," Expert Opinion on Drug Discovery, Jan. 1, 2012, 7(1):19-37.
Doyonnas et al., "Hematopoietic contribution to skeletal muscle regeneration by myelomoncytic precursors," Proc. Natl. Acad. Sci. U.S.A, 101:13507-13512 (2004).
Eatock and Rusch, "Developmental changes in the physiology of hair cells," Cell & Developmental Biology, 1997, 8:265-275.
Edge and Chen, "Hair cell regeneration," Curr Opin Neurobiol, 2008, 18: 377-382.
Edge et al., "Current Applications of Cellular Xenografts," Trans. Proc., 32:1169-1171 (2000).
Eng et al., "An approach to correlate tandem mass spectral data of peptides with amino acid sequences in a protein database," Journal of the American Society for Mass Spectrometry, 1994, 5:976-989.
EP Brief Communication in European Appln. No. 13836099.5, dated Jan. 19, 2021, 9 pages.
EP Extended Search Report in EP Appln. No. 17744987.3, dated Jul. 3, 2019, 9 pages.
EP Office Action in European Appln. No. 17744987, dated May 14, 2020, 3 pages.
Escobar-Chávez et al., "Applications of thermo-reversible pluronic F-127 gels in pharmaceutical formulations," J Pharm Pharm Sci., 2006, 9(3):339-58.
European Search Report in Application No. 13836099, dated Mar. 8, 2016, 9 Pages.
Examination Report issued in Australian Patent Application No. 2007334260 on Aug. 23, 2012 (5 pages).
Extended European Search Report issued in corresponding European Patent Application No. 07871464.9, mailed Nov. 17, 2010.
Extended European Search Report issued in EP 0982830, mailed Dec. 7, 2012.
Feng et al., "Blocking caspase-3-dependent pathway preserves hair cells from salicylate-induced apoptosis in the guinea pig cochlea," Mol Cell Biochem., 2011, 353:291-303.
Ferrer-Vaquer et al., "A sensitive and bright single-cell resolution live imaging reporter of Wnt/ss-catenin signaling in the mouse," BMC Dev Biol, Dec. 2010, 10:121, 18 pages.
Final Office Action issued in U.S. Appl. No. 13/130,607, filed Oct. 21, 2013, 11 pages.
Flora et al., "Deletion of Atohl disrupts Sonic Hedgehog signaling in the developing cerebellum and prevents medulloblastoma," Science, 2009, 326:1424-1427.
Flora et al., "The E-protein Tcf4 interacts with Math 1 to regulate differentiation of a specific subset of neuronal progenitors," PNAS, 2007, 104: 15382-15387.
Forge et al., "Hair Cell Recovery in the Vestibular Sensory Epithelia of Mature Guinea Pigs," The Journal of Comparative Neurology, 1998, 397: 69-88.
Forge et al., "Ultrastructural evidence for hair cell regeneration in the mammalian inner ear," Science, 1993, 259: 1616-1619.
Forget et al., "Shh Signaling Protects Atohl from Degradation Mediated By The E3 Ubiquitin Ligase Huwel In Neural Precursors," Developmental Cell, Jun. 2014, 29: 649-661.
Forneris et al., "Histone demethylation catalysed by LSD1 is a flavin-dependent oxidative process," FEBS Lett, Apr. 2005, 579(10):2203-2207.
Frisina, "Age-related hearing loss: ear and brain mechanisms," Annals of the New York Academy of Sciences, 2009, 1170: 708-717.
Fritzsch et al., "Atoh1 Null Mice Show Directed Afferent Fiber Growth to Undifferentiated Ear Sensory Epithelia Followed by Incomplete Fiber Retention," Dev. Dyn., 233:570-583 (2005).
Fritzsch et al., "Lack of Neurotrophin 3 Causes Losses of Both Classes of Spiral Ganglion Neurons in the Cochlea in a Region-Specific Fashion," J. Neurosci., 17:6213-6225 (1997).
Fritzsch, "Development of inner ear afferent connections: forming primaly neurons and connecting them to the developing sensory epithelia," Brain Research Bulletin, 2003, 60:423-433.
Fuerer and Nusse, "Lentiviral vectors to probe and manipulate the Wnt signaling pathway," PLoS One, 2010, 5(2):e9370, 7 pages.
Fujioka et al, "SY3A-H5 A novel y-secretase inhibitor, LY411575, replaced auditory hair cells and recovered hearing loss after severe acoustic trauma in mice," Neurosci Res., 2008, 61(Suppl):S25.
Fujioka et al., "In vivo differentiation toward hair cell: A novel gamma-secretase inhibitor, LY411575, replaced auditory hair cells and ameliorated hearing impairment after severe acoustic trauma in mice," Presented at The 31st Annual Meeting of the Japan Neuroscience Society Symposium "Regeneration of Sensory Cells in the Inner Ear—From Bench to Bedside, " Jul. 7, 2008, 30 pages.
Fujioka et al., "Manipulating cell fate in the cochlea: a feasible therapy for hearing loss," Trends Neurosci, 2015, 38: 139-144.
Gage, "Cell therapy," Nature, 392(6679 Suppl):18-24 (1998).
Gao et al., "mTOR drives its own activation via SCF(~TrCP)dependent degradation of the mTOR inhibitor DEPTOR," Molecular Cell, 2011, 44:290-303.
Gao et al., "Quantitative imaging of cochlear soft tissues in wild-type and hearingimpaired transgenic mice by spectral domain optical coherence tomography," Optics Express, 2011, 19:15415-15428.

(56) References Cited

OTHER PUBLICATIONS

Garapaty-Rao et al., "Identification of EZH2 and EZH1 Small Molecule Inhibitors with Selective Impact on Diffuse Large B Cell Lymphoma Cell Growth," Chem. Biol, 2013, 20(11):1329-1339.
Ge et al., "Distribution of PLGA nanoparticles in chinchilla cochleae," Otolaryngol Head Neck Surg., Oct. 2007, 137(4):619-23.
Geling et al., "A γ-secretase inhibitor blocks Notch signaling in vivo and causes a severe neurogenic phenotype in zebrafish," EMBO report, 2002, 688-694.
Geng et al., "Comprehensive Expression of Wnt Signaling Pathway Genes during Development and Maturation of the Mouse Cochlea, " PLoS One, Feb. 2016, 11(2):e0148339, 18 pages.
Gillespie et al., "LIF is more potent than BDNF in promoting neurite outgrowth of mammalian auditory neurons in vitro," Neuro. Rep., 12:275-279 (2001).
Golub et al., "Hair Cell Replacement in Adult Mouse Utricles after Targeted Ablation of Hair Cells with Diphtheria Toxin," The Journal of Neuroscience, Oct. 2012, 32: 15093-15105.
Gowan et al., "Crossinhibitory Activities of Ngn1 and Math1 Allow Specification of Distinct Dorsal Interneurons," Neuron., 31:219-232 (2001).
Goycoolea and Lundman, "Round window membrane. Structure function and permeability: a review," Microsc Res Tech., 36:201-11 (Feb. 1, 1997).
Gregorieff and Clevers, "Wnt signaling in the intestinal epithelium: from endoderm to cancer," Genes & Development, 2005, 19:877-890.
Groves, "The challenge of hair cell regeneration," Exp Biol Med (Maywood), Apr. 2010, 235(4):434-446.
Gubbels et al., "Functional auditory hair cells produced in the mammalian cochlea by in utero gene transfer," Nature, 2008, 455:537-541.
Guo et al., "Targeting the Notch signaling pathway in cancer therapeutics," Thoracic Cancer, 2014, 5: 473-486.
Haapasalo and Kovacs; "The Many Substrates of Presenilin/γ-Secretase" Journal Alzheimers Disease. 2011: 25(1): 3-28.
Hadland et al., "γ-secretase inhibitors repress thymocyte development," Proc Natl. Acad Sci USA, 98:7487-91 (Jun. 19, 2001).
Han and Shen, "Targeting γ-secretase in breast cancer," Breast Cancer: Targets and Therapy, 2012, 2012: 83-90.
Hanna et al., "Pluripotency and cellular reprogramming: facts, hypotheses, unresolved issues," Cell, Nov. 2010, 143(4):508-525.
Hartman et al., "Hes5 expression in the postnatal and adult mouse inner ear and the drug-damaged cochlea," J Assoc Res Otolaryngol., 10:321-40 (Sep. 2009).
Havenith et al., "Spiral ganglion cell survival after round window membrane application of brain-derived neurotrophic factor using gelfoam as carrier," Hearing Research, Feb. 2011, 272(1-2):168-177.
Hawkins et al., "The developmental genetics of auditory hair cells," Hum. Mol. Genet., 13:R289-296 (2004).
Heintzman et al., "Distinct and predictive chromatin signatures of transcriptional promoters and enhancers in the human genome," Nat Genet, Mar. 2007, 39(3):311-318.
Heller et al., "Parvalbumin 3 is an Abundant Ca2+ Buffer in Hair Cells," J. Assoc. Res. Otolaryngol., 3:488-498 (2002).
Helms et al., "Autoregulation and multiple enhancers control Math1 expression in the developing nervous system," Develop., 127:1185-1196 (2000).
Helms et al., "Overexpression of MATH1 Disrupts the Coordination of Neural Differentiation in Cerebellum Development," Mol. Cell. Neurosci., 17:671-682 (2001).
Hendrickx & Leyns, "Non-conventional Frizzled ligands and Wnt receptors," Develop Growth Differ., 2008, 50:229-243.
Hermann et al., "Efficient generation of neural stem cell-like cells from adult human bone marrow stromal cells," J. Cell. Sci., 117:4411-4422 (2004).
Herold et al., "Mizl and HectH9 regulate the stability of the checkpoint protein, TopBP1," The EMBO Journal, 2008, 27:2851-2861.

Herzog et al., "Plasticity of marrow-derived stem cells," Blood, 102:3483-3493 (2003).
Hess et al., "Bone marrow-derived stem cells initiate pancreatic regeneration," Nat. Biotechnol., 21:763-770 (2003).
Hildebrand et al, "Advances in Molecular and Cellular Therapies for Hearing Loss," Molecular Therapy, 2008, 16(2):224-236.
Hirabayashi et al., "The Wnt/beta-catenin pathway directs neuronal differentiation of cortical neural precursor cells," Development, 2004, 131: 2791-2801.
Hödar et al., "Genome-wide identification of new Wnt/beta-catenin target genes in the human genome using CART method," BMC Genomics, 2010, 11:348, 15 pages.
Horie et al., "Sustained delivery of lidocaine into the cochlea using poly lactic/glycolic acid microparticles," Laryngoscope, 2010, 120(2):377-83.
Hosoya et al., "Method for efficient screening of substances inducing differentiation into inner ear hair cells with the use of spheres derived from inner ear cells," Otol Jpn, 2008, 18(4): 275 (with English translation).
Hosoya et al., "An efficient screening method using inner-ear derived spheres for selection of compounds that induce hair cell differentiation," Neurosci. Res., 2008, 61S:S57 Abstract, 2 pages.
Hu and Ulfendahl, "Cell replacement therapy in the inner ear," Stem Cell and Development, 15:449-459 (2006).
Hu et al., "Diphtheria Toxin-Induced Cell Death Triggers Wnt-Dependent Hair Cell Regeneration in Neonatal Mice," J Neurosci, 2016, 36:9479-9489.
Hu et al., "Wnt/beta-catenin signaling in murine hepatic transit amplifying progenitor cells," Gastroenterology, Nov. 2007, 133(5):1579-1591.
Hu et al., "Neural cograft stimulates the survival and differentiation of embryonic stem cells in the adult mammalian auditory System," Brain Research, 2005, 1051:137-144.
Hu et al., "Survival and neural differentiation of adult neural stem cells transplanted into the mature inner ear," Exper. Cell. Res., 302:40-47 (2005).
Huang et al., "Lysine 63-linked polyubiquitination is required for EGF receptor degradation," PNAS, Sep. 2013, 110(39):15722-15727.
Huang, "Age-related hearing loss," Minn Med, 2007, 90(10):48-50.
Huibregtse et al., A family of proteins structurally and functionally related to the E6-AP ubiquitin-protein ligase, PNAS, 1995, 92:5249.
Hume et al., "Expression of LHX3 and SOX2 during mouse inner ear development," Gene Expression Patterns, 2007, 7:798-807.
Husseman and Raphael, Gene therapy in the inner ear using adenovirus vectors. Advances in Oto-Rhino-Laryngology, 2009, 66:37-51.
Huynh et al., "The novel gamma secretase inhibitor RO4929097 reduces the tumor initiating potential of melanoma," PLoS One, 6(9):e25264, (2011) 10 pages.
Hyde et al., "Studies to investigate the in vivo therapeutic window of the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY411,575) in the CRND8 mouse," J Pharmacol Exp Ther., 319:1133-43 (Dec. 2006).
Hyun et al., "In Vitro and in Vivo Release of Albumin Using a Biodegradable MPEG-PCL Diblock Copolymer as an in Situ Gel-Forming Carrier," Biomacromolecules, Apr. 2007, 8(4):1093-100.
Ikeda and Dikic, "Atypical ubiquitin chains: new molecular signals. "Protein Modifications: Beyond the Usual Suspects" review series," EMBO Reports, 2008, 9:536-542.
Inaoka et al., "Local application of hepatocyte growth factor using gelatin hydrogels attenuates noise-induced hearing loss in guinea pigs," Acta Otolaryngol., Apr. 2009, 129(4):453-7.
Incesulu and Nadal, "Correlation of acoustic threshold measures and spiral ganglion cell survival in severe to profound sensorineural hearing loss: implications for cochlear implantation," The Annals of Otology, Rhinology, and Laryngology, 1998, 107:906-911.
Inoue et al., "Mule/Huwel/Arf-BPI suppresses Ras-driven tumorigenesis by preventing c-Myc/Mizl-mediated down-regulation of p21 and p15," Genes & Development, 2013, 27: 1101-1114.
International Preliminary Report on Patentability for PCT/US2009/065747, issued May 24, 2011.

(56) References Cited

OTHER PUBLICATIONS

International Preliminary Report on Patentability in International Application No. PCT/US2013/058446, issued Mar. 10, 2015, 11 pages.
International Preliminary Report on Patentability in International Application No. PCT/US2016/064727, mailed on Jun. 14, 2018, 9 pages.
International Preliminary Report on Patentability in International Application No. PCT/US2017/015379, mailed on Aug. 9, 2018, 11 pages.
International Preliminary Report on Patentability in International Appln. No. PCT/US2019/063418, mailed on Jun. 10, 2021, 9 pages.
International Preliminary Report on Patentability issued in corresponding International Application No. PCT/US2007/084654, mailed May 28, 2009.
International Search Report and Written Opinion in International Application No. PCT/US15/43976, mailed on Jan. 20, 2016, 16 pages.
International Search Report and Written Opinion in International Application No. PCT/US2013/058446, mailed Dec. 26, 2013, 8 pages.
International Search Report and Written Opinion in International Application No. PCT/US2016/064727, mailed on May 1, 2017, 18 pages.
International Search Report and Written Opinion in International application No. PCT/US2017/015379, mailed on May 31, 2017, 18 pages.
International Search Report and Written Opinion in International Appln. No. PCT/US2019/063418, mailed on Apr. 23, 2020, 12 pages.
International Search Report issued in corresponding International Application No. PCT/US2007/84654, mailed Oct. 3, 2008.
Inuzuka et al., "SCFFBW7 regulates cellular apoptosis by targeting MCL1 for ubiquitylation and destruction," Nature, 2012, 470:104-109.
Invitation to Pay Additional Fees And, Where Applicable, Protest Fee in International Appln. No. PCT/US2019/063418, mailed on Feb. 24, 2020, 2 pages.
Ito et al., "Neurotrophins Facilitate Neuronal Differentiation of Cultured Neural Stem Cells Via Induction of mRNA Expression of Basic Helix-Loop-Helix Transcription Factors Mash1 and Math1," J. Neurosci. Res., 71:648-658 (2003).
Ivan et al., "HIFalpha targeted for VHL-mediated destruction by praline hydroxylation: implications for 02 sensing," Science, 2001,292:464-468.
Ivanov et al., "Genes required for *Drosophila* nervous system development identified by RNA interference," Proc. Nat. Acad. Sci., 101:16216-16221 (2004).
Izumikawa et al., "Auditory hair cell replacement and hearing improvement by Atoh1 gene therapy in deaf mammals," Nat Med., 11(3)271-6 (Mar. 2005).
Jaakkola et al., "Targeting of HIF-alpha to the von Hippel-Lindau ubiquitylation complex by 02-regulated prolyl hydroxylation," Science, 2001, 292:468-472.
Jacques et al., "A dual function for canonical Wnt/beta-catenin signaling in the developing mammalian cochlea," Development, Dec. 2012, 139(23):4395-4404, 18 pages.
Jaenisch and Bird, "Epigenetic regulation of gene expression: how the genome integrates intrinsic and environmental signals," Nat Genet, Mar. 2003, 33 Suppl:245-254.
Jahan et al., "Beyond generalized hair cells: molecular cues for hair cell types," Hear Res, Mar. 2013, 297:30-41.
Jarriault et al., "Delta-1 Activation of Notch-1 Signaling Results in HES-1 Transactivation," Mol. Cell. Biol, 1998, 18:7423-7431.
Jarriault et al., "Signalling downstream of activated mammalian Notch," Nature, 1995, 377:355-358.
Jeon et al., "Notch Signaling Alters Sensory or Neuronal Cell Fate Specification of Inner Ear Stem Cells," J. Neurosci, 2011, 31: 8351-8358.

Jeon et al., "Bone marrow mesenchymal stem cells are progenitors in vitro for inner ear hair cells," Molecular and Cellular Neurosciences, 34:59-68 (2007).
Jiang et al., "Neuroectodermal differentiation from mouse multipotent adult progenitor cells," Proc. Natl. Acad. Sci .U.S.A, 100:11854-11860 (2003).
Jiang et al., "Pluripotency of mesenchymal stem cells derived from adult marrow," Nature, 418:41-49 (2002).
Jin et al., "Systematic analysis and nomenclature of mammalian F-box proteins," Genes Dev, 2004, 18(21):2573-2580.
Jorstad et al., "Stimulation of functional neuronal regeneration from Müller glia in adult mice," Nature, Aug. 2017, 548(7665):103-107.
JP Office Action in Japanese Application No. 2017-132839, dated Jun. 18, 2019, 10 pages (with English translation).
JP Office Action in Japanese Appln. No. 2015-531223, dated Sep. 11, 2019, 5 pages (with English translation).
JP Office Action in Japanese Appln. No. 2015-531223, dated Jan. 5, 2021, 20 pages (with English translation).
JP Office Action in Japanese Appln. No. 2019-091552, dated Apr. 28, 2020, 8 pages (with English translation).
JP Office Action in Japanese Appln. No. 2019-228284, dated Jan. 26, 2021, 5 pages (with English translation).
Kaneko et al., "Musashi1: an evolutionally conserved marker for CNS progenitor cells including neural stem cells," Dev Neurosci., 22:139-53 (2000).
Kawamoto et al., "Spontaneous hair cell regeneration in the mouse utricle following gentamicin ototoxicity," Hearing Research, 2009, 247: 17-26.
Kearns et al., "Functional annotation of native enhancers with a Cas9-histone demethylase fusion," Nat Methods, 2015, 12:401-403, 6 pages.
Kehrle et al., "Comparison of Auditory Brainstem Response Results in Normal-Hearing Patients With and Without Tinnitus," Arch Otolaryngol Head Neck Surg., 2008, 134(6):647-651.
Kelley et al., "Regulation of cell fate in the sensory epithelia of the inner ear," Nat Rev Neurosci, 2006, 7: 837-849.
Kerenyi et al., "Histone demethylase LSD1 represses hematopoietic stem and progenitor cell signatures during blood cell maturation," eLife, 2013, 2:e00633, 23 pages.
Kicic et al., "Differentiation of Marrow Stromal Cells into Photoreceptors in the Rat Eye," J. Neurosci., 23:7742-7749 (2003).
Kiernan et al., "Sox2 is required for sensory organ development in the mammalian inner ear," Nature, 434:1031-1035 (2005).
Kim et al., "Dopamine neurons derived from embryonic stem cells function in an animal model of Parkinson's disease," Nature, 418:50-6 (2002).
Kim et al., "NeuroD-null mice are deaf due to a severe loss of the inner ear sensory neurons during development," Develop., 128:417-426 (2001).
Klisch et al., "In vivo Atoh1 targetome reveals how a proneural transcription factor regulates cerebellar development," PNAS, 2011, 108(8):3288-3293.
Knippschild et al., "Metaanalysis to Estimate the Expected Drop Out-Rates Reported in Clinical Trials on Cataract Surgery," 2014, 231: 151-157 (with English abstract).
Knippschild et al., "The CK1 family: contribution to cellular stress response and its role in carcinogenesis," Frontiers in Oncology, May 2014, 4: 32 pages.
Koch et al., "The landscape of histone modifications across 1% of the human genome in five human cell lines," Genome Res, 2007, 17(6):691-707.
Kondo et al., "Sonic Hedgehog and retinoic acid synergistically promote sensory fate specification from bone marrow-derived pluripotent stem cells," Proc. Natl. Acad. Sci. U.S.A., 102(13):4789-4794 (Mar. 2005).
Kondo et al., "Wnt Signaling Promotes Neuronal Differentiation From Mesenchymal Stem Cells Through Activation of Tlx3," Stem Cells, 2011, 29(5):836-46.
Kopan et al., "The Canonical Notch Signaling Pathway: Unfolding the Activation Mechanism," Cell, 2009, 137:216-233.
Kurokawa et al., "A network of substrates of the E3 ubiquitin ligases MDM2 and HUWEI control apoptosis independently of p53," Science Signaling, 2013, 6:ra32.

(56) References Cited

OTHER PUBLICATIONS

Lanford et al., "Notch signalling pathway mediates hair cell development in mammalian cochlea," Nature Genetics, 21:289-292 (1999).
Lang et al., "Contribution of Bone Marrow Hematopoietic Stem Cells to Adult Mouse Inner Ear: Mesenchymal Cells and Fibrocytes," J .Comp. Neurol., 496:187-201 (2006).
Lanzoni et al., "MDL 28170 Attenuates Gentamicin Ototoxicity," Audiological Medicine, 2005, 3:82-89.
Latres et al., "The human F box protein beta-Trcp associates with the Cull/Skpl complex and regulates the stability ofbeta-catenin," Oncogene, Jan. 1999, 18:849-854.
Laurent et al., "A specific LSD1/KDM1A isoform regulates neuronal differentiation through H3K9 demethylation," Mol Cell, Mar. 2015, 57(6):957-970.
Ledent et al., "Phylogenetic analysis of the human basic helix-loop-helix proteins," Genome Biology, 2002, 3:research0030.1.
Lee et al., "Proteasome inhibitors induce auditory hair cell death through peroxisome dysfunction," Biochem. Biophys. Res. Comm., Jan. 2015, 456(1):269-274.
Lee et al., "Efficient generation of midbrain and hindbrain neurons from mouse embryonic stem cells," Nat. Biotech., 18:675-9, (2000).
Lee et al., "EZH2 generates a methyl degron that is recognized by the DCAF1/DDB1/CUL4 E3 ubiquitin ligase complex," Molecular Cell, 2012, 48:572-586.
Lei et al., "Lysine-specific demethylase 1 promotes the sternness and chemoresistance of Lgr5(+) liver cancer initiating cells by suppressing negative regulators of beta-catenin signaling," Oncogene, Jun. 2015, 34(24):3188-98.
Leon et al., "Insulin-Like Growth Factor-I Regulates Cell Proliferation in the Developing Inner Ear, Activating Glycosyl-Phosphatidylinositol Hydrolysis and Fos Expression," Endocrinol., 136:3494-3503 (1995).
Li et al., "Round Window Membrane Delivery of L-Methionine Provides Protection from Cisplatin Ototoxicity Without Compromising Chemotherapeutic Efficacy," Neuro Toxicology, 2001, 22:163-176.
Li et al., "Correlation of Pax-2 Expression with Cell Proliferation in the Developing Chicken Inner Ear," J. Neurobiol., 60:61-70 (2004).
Li et al., "Generation of hair cells by stepwise differentiation of embryonic stem cells," Proc. Natl. Acad. Sci. U.S.A. Nov. 2003, 100(23):13495-13500.
Li et al., "Pluripotent stem cells from the adult mouse inner ear," Nat. Med., 9:1293-1299 (2003).
Li et al., "Specification of motoneurons from human embryonic stem cells," Nat. Biotechnol., 23:215-21 (2005).
Li et al., "Stem cells as therapy for hearing loss," Trends Mol. Med., 10:309-315 (2004).
Lin et al., "Hair cell damage recruited Lgr5-expressing cells are hair cell progenitors in neonatal mouse utricle," Front Cell Neurosci, Apr. 2015, 9: 1-11.
Lin et al., "Inhibition of notch activity promotes non-mitotic regeneration of hair cells in the adult mouse utricles," J Neurosci., 31(43):15329-15339 (Oct. 26, 2011).
Lo et al., "Mammalian achaete-scute homolog 1 is transiently expressed by spatially restricted subsets of early neuroepithelial and neural crest cells," Genes & Development, 1991, 5: 1524-1537.
Loo et al., "From short peptides to nanofibers to macromolecular assemblies in biomedicine," Biotechnol Adv., 2012, 30(3):593-603.
Loseva et al, "Comparison of reactive processes in the rat brain elicited by xenotransplantation of nervous tissues of chicken or pulmonate snail," Brain Research, 2001, 915:125-132.
Love et al., "Moderated estimation of fold change and dispersion for RNA-seq data with DESeq2," Genome Biol, 2014, 15(12):550, 21 pages.
Lu et al., "Abstract #: 774: The Influence of Glycogen Synthase Kinase 3 On Cell Proliferation in the Murine Vestibular Sensory Epithelium," ARO 31st Annual Midwinter Meeting, Phoenix, Arizona, Feb. 16-21, 2008, 3 pages.

Lu et al., "The Influence of Glycogen Synthase Kinase 3 in Limiting Cell Addition in the Mammalian Ear," Develop. Neurobiol., 68:1059-1075 (2008).
Luistro et al., "Preclinical Profile of a Potent γ-Secretase Inhibitor Targeting Notch Signaling with In vivo Efficacy and Pharmacodynamic Properties," Cancer Res, Oct. 2009, 69(19):7672-7690.
Lumpkin et al., "Math1-driven GFP expression in the developing nervous system of transgenic mice," Gene Expr Patterns, 3:389-95 (Aug. 2003).
Ma and Raible, "Signaling pathways regulating zebrafish lateral line development," Current Biology, 2009, 19:R381-386.
Ma et al., "Neurogenin 1 Null Mutant Ears Develop Fewer, Morphologically Normal Hair Cells in Smaller Sensory Epithelia Devoid of Innervation," Assoc. Res. Otolaryngol., 1:129-143 (2000).
Madisen et al., "A robust and high-throughput Cre reporting and characterization system for the whole mouse brain," Nat Neurosci, 2010, 13: 133-140.
Maiques-Diaz et al., "Enhancer Activation by Pharmacologic Displacement of LSD1 from GFI1 Induces Differentiation in Acute Myeloid Leukemia," Cell Rep, Mar. 2018, 22:3641-3659, 40 pages.
Maksimovic et al., "Epidermal Merkel cells are mechanosensory cells that tune mammalian touch receptors," Nature, 2014, 509:617-621.
Mangi et al., "Mesenchymal stem cells modified with Akt prevent remodeling and restore performance of infarcted hearts," Nat. Med., 9:1195-201 (2003).
Markkanen et al., "Regulation of oxidative DNA damage repair by DNA polymerase A and MutYH by cross-talk of phosphorylation and ubiquitination," PNAS, 2012, 109:437-442.
Maru et al., "Lentivirus-Based Stable Gene Delivery into Intestinal Organoids," Methods Mol Biol, 2016, 1422:13-21.
Masuda et al., "Dual antitumor mechanisms of notch signaling inhibitor in a T-cell acute lymphoblastic leukemia xenograft model," Cancer Sci., 100(12):2444-2450 (Dec. 2009).
Matei et al., "Smaller Inner Ear Sensory Epithelia in Neurog1 Null Mice Are Related to Earlier Hair Cell Cycle Exit," Dev. Dyn., 234:633-50 (2005).
Matsui et al., "Regeneration and replacement in the vertebrate inner ear," Drug Discov. Today, 10:1307-12 (2005).
Matsuoka et al, In Vivo and In Vitro Characterization of Bone Marrow-Derived Stem Cells in the Cochlea, Laryngoscope, Aug. 2006, 116:1363-1367.
McLean et al., "Clonal Expansion of Lgr5-Positive Cells from Mammalian Cochlea and High-Purity Generation of Sensory Hair Cells," Cell Reports, Feb. 2017, 18(8):1917-1929.
Meierhofer et al., "Quantitative analysis of global ubiquitination in HeLa cells by mass spectrometry," Journal of Proteome Research, 2008, 7:4566-4576.
Metzger et al., "LSD1 demethylates repressive histone marks to promote androgen-receptor-dependent transcription," Nature, Sep. 2005, 437(7057):436-439, 5 pages.
Mezey et al., "Transplanted bone marrow generates new neurons in human brains," Proc. Natl. Acad. Sci. U.S.A., 100:1364-1369 (2003).
Miesegaes et al., "Identification and subclassification of new Atohl derived cell populations during mouse spinal cord development," Developmental Biology, Mar. 2009, 327:339-351.
Mikulec et al., "Permeability of the round window membrane is influenced by the composition of applied drug solutions and by common surgical procedures," Otol Neurotol., 29:1020-6 (Oct. 2008).
Mitani et al., "Differential Effects between γ-Secretase Inhibitors and Modulators on Cognitive Function in Amyloid Precursor Protein-Transgenic and Nontransgenic Mice," J. Neuroscience, Feb. 2012.
Mizutari et al., "Notch inhibition induces cochlear hair cell regeneration and recovery of hearing after acoustic trauma," Neuron, 2013, 77: 58-69.
Moon et al., "WNT and B-catenin signalling: diseases and therapies," Nature Reviews, Sep. 2004, 5: 689-699.
Moore et al., "Modulation of Wnt Signaling Through Inhibition of Secreted Frizzled-Related Protein I (sFRP-1) with N-Substituted Piperidinyl Diphenylsulfonyl Sulfonamides," J Med.Chem., 2009, 52(1):105-116.

(56) References Cited

OTHER PUBLICATIONS

Morrison et al., "Mammalian Merkel cells are descended from the epidermal lineage," Developmental Biology, 2009, 336:76-83.
Murre et al., "Interactions between heterologous helixloop-helix proteins generate complexes that bind specifically to a common DNA sequence.," Cell, 1989, 58:537-544.
Murry et al., "Haematopoietic stem cells do not transdifferentiate into cardiac myocytes in myocardial infarcts," Nature., 428:664-668 (2004).
Nadol, Jr. et al., "Degenerative Changes in the Organ of Corti and Lateral Cochlear Wall in Experimental Endolymphatic Hydrops and Human Meniere's Disease," Acta Otolaryngol, 1995, Suppl 519: 47-59.
Naito Yasushi et al., "Transplantation of bone marrow stromal cells into the cochlea of chinchillas," NeuroReport, Lippincott Williams & Wilkins, 15:1-4 (2004).
Nakagawa, "Aiming for the treatment of inner ear diseases—the forefront of basic research," Bulletin of the Japan Otolaryngology Society, 2008, 11(10):655-663 (with machine abstract).
Naujokat and Saric, "Concise review: role and function of the ubiquitinproteasome system in mammalian stem and progenitor cells," Stem Cells, 2007, 25 :2408-2418.
Non-Final Office Action issued in U.S. Appl. No. 13/130,607, filed Apr. 19, 2013, 11 pages.
Non-Final Office Action issued in U.S. Appl. No. 13/130,607, filed Oct. 23, 2014, 12 pages.
Notice of Opposition to European Patent in European Application No. 09828380.7, dated Jan. 11, 2018, 39 pages.
Noy et al., "HUWE1 ubiquitinates MyoD and targets it for proteasomal degradation," Biochemical and Biophysical Research Communications, 2012, 418:408-413.
Ocampo et al., "In Vivo Amelioration of Age-Associated Hallmarks by Partial Reprogramming," Cell, Dec. 2016, 167(7):1719-1733. e12, 28 pages.
Oesterle et al., "Sox2 and JAGGED1 expression in normal and drug-damaged adult mouse inner ear," J Assoc Res Otolaryngol., 9:65-89 (Mar. 2008).
Office Action in European Application No. 13836099.5, dated Jul. 25, 2018, 5 pages.
Office Action in Japanese Application No. 2015-178811, dated Jun. 5, 2018, 12 pages (with English translation).
Office Action in Japanese Application No. 2015-178811, dated Oct. 17, 2017, 6 pages (with English translation).
Office Action in Japanese Application No. 2015-531223, dated Jan. 15, 2019, 6 pages (with English translation).
Office Action in Japanese Application No. 2015-531223, dated Jul. 11, 2017, 8 pages (with English translation).
Office Action in Japanese Application No. 2015-531223, dated Jun. 19, 2018, 7 pages (with English translation).
Office Action issued in AU2009316264 on Jan. 16, 2015 (5 pages).
Office Action issued in CA2,669,693 on Apr. 4, 2014 (4 pages).
Office Action issued in EP07871464.9 on May 6, 2014 (5 pages).
Office Action issued in European Application No. 09828380.7 on Mar. 26, 2014 (6 pages).
Office Action issued in Japanese Application No. 2011-537715 issued on Feb. 4, 2014 (translation) 4 pages.
Office Action issued in JP2009-537328 on Feb. 12, 2013 (7 pages).
Office Action issued in JP2011-537715 on Jan. 20, 2015 with English translation (7 pages).
Office Action issued in JP2015-178811 on Mar. 7, 2017 with English translation (5 pages).
Ohyama et al., "Wnt signals mediate a fate decision between otic placode and epidermis," Development, 2006, 133:865-875.
Okubo and Hogan, "Hyperactive Wnt signaling changes the developmental potential of embryonic lung endoderm," Journal of Biology, 2004, 3: 11.
Orford et al., "Differential H3K4 methylation identifies developmentally poised hematopoietic genes," Dev Cell, May 2008, 14(5):798-809.
Oshima et al., "Differential distribution of stem cells in the auditory and vestibular organs of the inner ear," J Assoc Res Otolaryngol., 8:18-31 (Mar. 2007).
Oshima et al., "Mechanosensitive hair cell-like cells from embryonic and induced pluripotent stem cells," Cell, 2010, 141(4): 704-716.
Pagani et al., "Autologous Skeletal Myoblasts Transplanted to Ischemia-Damaged Myocardium in Humans," J. Am. Coll. Cardiol., 41:879-888 (2003).
Pan et al., "Understanding the evolution and development of neurosensory transcription factors of the ear to enhance therapeutic translation," Cell Tissue Res, Jun. 2012, 349:415-432.
Pan et al., "A novel Atoh1 "self-terminating" mouse model reveals the necessity of proper Atoh1 level and duration for hair cell differentiation and viability," PloS One, 2012, 7:e30358.
Pandya et al., "A structural element within the HUWE1 HECT domain modulates self-ubiquitination and substrate ubiquitination activities," The Journal of Biological Chemistry, 2010, 285:5664-5673.
Park et al., "H3K27 Demethylase JMJD3 Employs the NF-kappaB and BMP Signaling Pathways to Modulate the Tumor Microenvironment and Promote Melanoma Progression and Metastasis," Cancer Res, Jan. 2016, 76(1):161-170.
Parker et al., "An independent construct for conditional expression of atonal homolog-1," Human Gene Therapy Methods, 2014, 25:1-13.
Parker et al., "Primary culture and plasmid electroporation of the murine organ of Corti," Journal of Visualized Experiments, 2010.
Parker, "Biotechnology in the treatment of sensorineural hearing loss: foundations and future of hair cell regeneration," Journal of Speech, Language, and Hearing Research, 2011, 54: 1 709-1731.
Patel et al., "The histone demethylase LSD1 regulates inner ear progenitor differentiation through interactions with Pax2 and the NuRD repressor complex," PLoS One, Jan. 2018, 13(1):e0191689, 20 pages.
Patzel et al., "Design of siRNAs producing unstructured guide-RNAs results in improved RNA interference efficiency," Nature Biotechnol., 23:1440-1444 (2005).
Pauley et al., "Expression and Function of FGF10 in Mammalian Inner Ear Development," Dev. Dyn., 227:203-215 (2003).
Paulson et al., "A Novel Controlled Local Drug Delivery System for Inner Ear Disease," Laryngoscope, Apr. 2008, 118(4):706-11.
Pedersen, "Cells for Medicine," Scientif. Am., 280:68-73 (1999).
Peng et al., "A proteomics approach to understanding protein ubiquitination," Nature Biotechnology, 2003, 21:921-926.
Petit, "Usher syndrome: from genetics to pathogenesis," Annu Rev Genomics Hum Genet., 2:271-97 (2001).
Pickart, "Ubiquitin enters the new millennium," Molecular Cell, Sep. 2001, 8(3):499-504.
Pirvola et al., "Neurotrophic Factors during Inner Ear Development," Curr. Top. Dev. Biol., 57:207-223 (2003).
Pittenger et al., "Multilineage Potential of Adult Human Mesenchymal Stem Cells," Sci., 284:143-147 (1999).
Piu et al., "OTO-104: A Sustained-Release Dexamethasone Hydrogel for the Treatment of Otic Disorders," Otol Neurotol., Jan. 2011, 32(1):171-9.
Plum et al., "Connexin31-deficiency in mice causes transient placental dysmorphogenesis but does not impair hearing and skin differentiation," Dev Biol., 231:334-47 (2001).
Presente et al., "Notch is required for long-term memory in *Drosophila*," Proc. Nat. Acad. Sci., 101:1764-1768 (2004).
Price, "CKI, there's more than one: casein kinase I family members in Wnt and Hedgehog signaling," Genes & Development, 20: 399-410.
Purow et al., "Expression of Notch-1 and Its Ligands, Delta-Like-1 and Jagged-1, Is Critical for Glioma Cell Survival and Proliferation," Cancer Res., 65:2353-2363 (2005).
Qyang et al., "The renewal and differentiation of Isl 1 + cardiovascular progenitors are controlled by a Wnt/beta-catenin pathway," Cell Stem Cell, 2007, 1: 165-179.

(56) References Cited

OTHER PUBLICATIONS

Railo et al., "Genomic response to Wnt signalling is highly context-dependent—evidence from DNA microarray and chromatin immunoprecipitation screens ofWnt/TCF targets," Exp Cell Res, Oct. 2009, 315(26):2690-2704.
Rask-Andersen et al., "Regeneration of human auditory nerve. In vitro/in video demonstration of neural progenitor cells in adult human and guinea pig spiral ganglion," Hear. Res., 203:180-191 (2005).
Ravid and Hochstrasser, "Diversity of degradation signals in the ubiquitin-proteasome system," Nat Rev Mol Cell Biol, 2008, 9(9):679-90.
RCE and Response to Final Office Action issued in U.S. Appl. No. 13/130,607, filed Apr. 21, 2014, 8 pages.
Rena et al., "D4476, a cell-permeant inhibitor of CKI, suppresses the site-specific phosphorylation and nuclear exclusion of FOXO1a," EMBO reports, 2004, 5: 60-65.
Response to Non-Final Office Action issued in U.S. Appl. No. 13/130,607, filed Jul. 19, 2013, 5 pages.
Response to Non-Final Office Action issued in U.S. Appl. No. 13/130,607, filed Oct. 23, 2014 and Apr. 23, 2015 (10 pages).
Response to Restriction Requirement issued in U.S. Appl. No. 13/130,607, filed Dec. 12, 2012, 2 pages.
Response to Restriction Requirement issued in U.S. Appl. No. 13/759,441, filed Dec. 22, 2014 and Mar. 19, 2015 (4 pages).
Response to U.S. Final Office Action in U.S. Appl. No. 13/130,607, dated Jan. 15, 2016, 9 pages.
Restriction Requirement issued in U.S. Appl. No. 13/130,607, filed Oct. 12, 2012, 13 pages.
Restriction Requirement issued in U.S. Appl. No. 13/759,441, filed Dec. 22, 2014 (4 pages).
Riccomagno et al., "Wnt-dependent regulation of inner ear morphogenesis is balanced by the opposing and supporting roles of Shh," Genes & Development, 2005, 19: 1612-1623.
Roberson et al., "Direct transdifferentiation gives rise to the earliest new hair cells in regenerating avian auditory epithelium," Journal of Neuroscience Research, 2004,7 8: 461-4 71.
Roccio et al., "Cell cycle reactivation of cochlear progenitor cells in neonatal FUCCI mice by a GSK3 small molecule inhibitor," Sci Rep, Dec. 2015, 5: 1-11.
Ross et al., "Basic helix-loop-helix factors in cortical development," Neuron, Jul. 2003, 39: 13-25.
Rotin and Kumar, "Physiological functions of the HECT family of ubiquitin Ligases," Nature Reviews Molecular Cell Biology, 2009, 10:398-409.
Rubel et al., "Mammalian Vestibular Hair Cell Regeneration," Science, Feb. 1995, 267(5198):701-707.
Ryals and Rubel, "Hair Cell Regeneration After Acoustic Trauma in Adult Coturnix Quail," Science, Jun. 1988, 240:1774-1776.
Ryusuke et al., "Pharmacological inhibition of Notch signaling in the mature guinea pig cochlea" Neuroreport, Lippincott Williams and Wilkins, UK, Dec. 2007, 18(18): 1911-1914.
Sakaguchi et al., "Spatiotemporal patterns of Musashi1 expression during inner ear development," Neuroreport, 15:997-1001 (Apr. 29, 2004).
Sakamoto et al., "Inner ear drug delivery system from the clinical point of view," Acta Otolaryngol Suppl., Nov. 2010, 563:101-4.
Sakamoto et al., "Fates of mouse embryonic stem cells transplanted into the inner ears of adult mice and embryonic chickens," Acta Otolarynol Suppl., 551:48-52 (2004).
Salt and Plontke, "Principles of local drug delivery to the inner ear," Audiol Neurootol., 14:350-60 (2009).
Samarajeewa et al., "Transcriptional response to Wnt activation regulates the regenerative capacity of the mammalian cochlea," Development, Nov. 2018, 145(23):dev166579, 27 pages.
Samon et al., "Preclinical analysis of the γ-secretase inhibitor PF-03084014 in combination with glucocorticoids in T-cell acute lymphoblastic leukemia," Mol Cancer Ther., 11(7):1565-1575 (Jul. 2012).

Samstein and Platt, "Physiologic and immunologic hurdles to xenotransplantation," Journal of American Society of Nephrology, 12:182-193 (2001).
Sarrazin et al., "Proneural gene requirement for hair cell differentiation in the zebrafish lateral line," Dev. Biol., 295:534-545 (2006).
Satoh and Fekete, "Clonal analysis of the relationships between mechanosensory cells and the neurons that innervate them in the chicken ear," Develop., 132:1687-1697 (2005).
Scheffner and Staub, "HECT E3s and human disease," BMC Biochemistry, Nov. 2007, 8 Suppl 1:S6.
Schwarz et al., "Characterization of human hect domain family members and their interaction with UbcH5 and UbcH7," The Journal of Biological Chemistry, 1998, 273: 12148-12154.
Shakoori et al., "Deregulated GSK3b activity in colorectal cancer: Its association with tumor cell survival and proliferation," Biochem and Biophys Research Comm, 2005, 334: 1365-1373.
Shi et al., "Abstract #: 732: Interaction of B-Catenin with an Atoh1 3' Enhancer Upregulates Atoh1 Expression and Increases Differentiation of Progenitors to Hair Cells," ARO 32nd Annual Midwinter Meeting, Baltimore, Maryland, Feb. 14-19, 2009, 3 pages.
Shi et al., "Generation of hair cells in neonatal mice by beta-catenin overexpression in Lgr5-positive cochlear progenitors," PNAS, 2013, 110: 13851-13856.
Shi et al., "Wnt-responsive lgr5-expressing stem cells are hair cell progenitors in the cochlea," J Neurosci, 2012, 32: 9639-9648.
Shi et al., "β-Catenin Up-regulates Atoh1 Expression in Neural Progenitor Cells by Interaction with an Atoh1 3' Enhancer," J Biol Chem, Jan. 2010, 285(1):392-400.
Shi et al., "β-Catenin Is Required for Hair-Cell Differentiation in the Cochlea," The Journal of Neuroscience, 2014, 34:6470-6479.
Skowyra et al., "F-box proteins are receptors that recruit phosphorylated substrates to the SCF ubiquitin-ligase complex," Cell, 1997, 91:209-219.
Sowa et al., "Defining the human deubiquitinating enzyme interaction landscape," Cell, 2009, 138:389-403.
Sparling et al., "Adipocyte-specific blockade of gamma-secretase, but not inhibition of Notch activity, reduces adipose insulin sensitivity," Molecular Metabolism, 2016, 5: 113-121.
Spence et al., "A ubiquitin mutant with specific defects in DNA repair and multiubiquitination," Molecular and Cellular Biology, 1995, 15:1265-1273.
Staecker et al., "Vestibular hair cell regeneration and restoration of balance function induced by math1 gene transfer," Otology & Neurotology, 2007, 28:223-231.
Stahle et al., "Long-term Progression of Meniere's Disease," Acta Otolaryngol, 1991, Suppl. 485: 78-83.
Stallwood et al., "Small Interfering RNA-Mediated Knockdown of Notch Ligands in Primary CD4+ T Cells and Dendritic Cells Enhances Cytokine Production," J. Immunol., 177:885-895 (2006).
Stambolic et al., "Lithium inhibits glycogen synthase kinase-3 activity and mimics Wingless signalling in intact cells," Current Biology, 1996, 6: 1664-1668.
Stevens et al., "Forced activation of Wnt signaling alters morphogenesis and sensory organ identity in the chicken inner ear, " Dev. Biol, 2003, 261: 149-164.
Stojanova et al., "Epigenetic regulation of Atoh1 guides hair cell development in the mammalian cochlea," Development, 2015, 142(20):3529-3536.
Stone and Cotanche, "Identification of the timing of S phase and the patterns of cell proliferation during hair cell regeneration in the chick cochlea," The Journal of Comparative Neurology, 1994, 341:50-67.
Subramanian et al., "Gene set enrichment analysis: a knowledge-based approach for interpreting genome wide expression profiles," PNAS, Oct. 2005, 102(43):15545-15550.
Sumitran et al, "Porcine Embryonic Brain Cell Cytotoxicity Mediated by Human Natural Killer Cells," Cell Transplantation, 1999, 601-610.
Sun et al., "Histone demethylase LSD1 regulates neural stem cell proliferation," Mol Cell Biol, Apr. 2010, 30(8):1997-2005.
Supplementary European Search Report issued in EP09828380 on Nov. 30, 2012 (8 pages).

(56) References Cited

OTHER PUBLICATIONS

Swan et al., "Inner ear drug delivery for auditory applications," Advanced Drug Delivery Reviews, 2008, 60: 1583-1599.
Sziklai et al., "Otosclerosis: an organ-specific inflammatory disease with sensorineural hearing loss," Eur. Arch. Otorhinolaryngol., 2009, 266:1711-1718.
Tai and Schuman, "Ubiquitin, the proteasome and protein degradation in neuronal function and dysfunction," Nature Reviews Neuroscience, 2008, 9:826-838.
Takebayashi et al., "Multiple roles of Notch signaling in cochlear development," Developmental Biology, 2007, 307: 165-178.
Tamura et al., "Drug Delivery to the Cochlea Using PLGA Nanoparticles," Laryngoscope, Nov. 2005, 115(11):2000-5.
Tan et al., "Parallel SCF adaptor capture proteomics reveals a role for SCFFBXL17 in NRF2 activation via BACH1 repressor turnover," Molecular Cell, 2013, 52:9-24.
Tiveron et al., "Role of Phox2b and Mash1 in the generation of the vestibular efferent nucleus," Developmental Biology, 2003, 260:46-57.
Tsuchiya et al., "Reciprocal targeting ofHath1 and beta-catenin by Wnt glycogen synthase kinase 3beta in human colon cancer," Gastroenterology, 2007, 132:208-220.
U.S. Final Office Action in U.S. Appl. No. 13/130,607, dated Jan. 15, 2016, 26 pages.
Varshavsky, "Naming a targeting signal," Cell, 1991, 64:13-15.
Vats et al, "Stem cells: sources and applications," Clin. Otoaryngol, 2002, 27:227-232.
Vierbuchen et al., "Direct conversion of fibroblasts to functional neurons by defined factors," Nature, 463:1035-41 (Feb. 25, 2010).
Wagers et al., "Little Evidence for Developmental Plasticity of Adult Hematopoietic Stem Cells," Science, 297:2256-2259 (2002).
Wagner and Jung, "New lysine methyltransferase drug targets in cancer," Nature Biotechnology, 2012, 30:622-623.
Wang et al., "Dose-dependent sustained release of dexamethasone in inner ear cochlear fluids using a novel local delivery approach," Audiol Neurootol., 2009, 14(6):393-401.
Wang et al., "LSD1 co-repressor Rcor2 orchestrates neurogenesis in the developing mouse brain," Nat Commun, Jan. 2016, 7:10481, 14 pages.
Wang et al., "Principles of inner ear sustained release following intratympanic administration," Laryngoscope, Feb. 2011, 121(2):385-91.
Wang et al., "Cell fusion is the principal source of bone-marrow-derived hepatocytes," Nature, 422:897-901 (2003).
Wang et al., "Dynamics of noise-induced cellular injury and repair in the mouse cochlea," J Assoc Res Otolaryngol., 3:248-68 (Sep. 2002).
Wang et al., "HUWE1 interacts with BRCA1 and promotes its degradation in the ubiquitin-proteasome pathway," Biochemical and Biophysical Research Communications, 2013.
Warchol et al., "Regenerative proliferation in inner ear sensory epithelia from adult guinea pigs and humans," Science, 1993, 259: 1619-1622.
Warner et al., "Expression of ZIC Genes in the Development of the Chick Inner Ear and Nervous System," Dev. Dyn., 226:702-712 (2003).
Watanabe et al., "Conditioned mesenchymal stem cells produce pleiotropic gut trophic factors," J Gastroenterol, 2014, 49:270-282, 13 pages.
Web.Stanford.Edu [online], "Wnt Target genes," 2018, retrieved on Sep. 9, 2022, retrieved from URL<web.stanford.edu/group/nusselab/cgi-bin/wnt/target_genes>, 4 pages.
Weimann et al., "Contribution of transplanted bone marrow cells to Purkinje neurons in human adult brains," Proc. Natl. Acad. Sci. U.S.A., 100:2088-2093 (2003).
White et al., "Mammalian cochlear supporting cells can divide and trans-differentiate into hair cells," Nature, 441:984-987 (2006).
Whyte et al., "Enhancer decommissioning by LSD1 during embryonic stem cell differentiation," Nature, Feb. 2012, 482(7384):221-225.
Wislet-Gendebien et al., "Plasticity of cultured mesenchymal stem cells: switch from nestin-positive to excitable neuron-like phenotype," Stem Cells, 2005, 23:392-402.
Wolfe, "γ-secretase Inhibition and Modulation for Alzheimer's Disease," Curr Alzheimer Res., 5(2):158-164 (Apr. 2008) (Author Manuscript).
Wong et al., "Chronic treatment with the gamma-secretase inhibitor L Y-411,575 inhibits beta-amyloid peptide production and alters lymphopoiesis and intestinal cell differentiation," J Biol Chem., 279:12876-82 (Mar. 26, 2004).
Woods et al., "Math1 regulates development of the sensory epithelium in the mammalian cochlea," Nat. Neurosci., 7:1310-1318 (2004).
Written Opinion of the International Searching Authority for PCT/US2009/065747, mailed Apr. 8, 2010, 3 pages.
Written Opinion of the International Searching Authority issued in corresponding International Application No. PCT/US2007/84654, mailed Oct. 3, 2008, 5 pages.
Wu et al., "A systematic survey of carbonic anhydrase mRNA expression during mammalian inner ear development," Dev Dyn, Mar. 2013, 242(3):269-280.
Wu et al., "Structure of a beta-TrCP 1-Skp 1-beta-catenin complex: destruction motif binding and lysine specificity of the SCF(beta-TrCP 1) ubiquitin ligase," Molecular Cell, 2003, 11:1445-1456.
Xia et al., "Ototoxicity of cisplatin administered to guinea pigs via the round window membrane," J Toxicol Sci., 2012, 37(4):823-830.
Yamada et al., "Rest promotes the early differentiation of mouse ESCs but is not required for their maintenance," Cell Stem Cell, Jan. 2010, 6(1):10-15.
Yamamoto et al., "Inhibition of Notch/RBP-J signaling induces hair cell formation in neonate mouse cochleas," J. Mol. Med., 84(1):37-45 (Jan. 2006).
Yang et al., "EGb 761 (Ginkgo biloba) protects cochlear hair cells against ototoxicity induced by gentamicin via reducing reactive oxygen species and nitric oxide-related apoptosis," J Nutr Biochem., 2011, 22:886-894.
Yang et al., "E3 ubiquitin ligase Mule ubiquitinates Miz1 and is required for TNFalphainduced INK activation," PNAS, 2010, 107:13444-13449.
Yang et al., "Generation and characterization of Atoh1-Cre knock-in mouse line," Genesis, 2010, 48:407-413.
Yang et al., "Requirement of Math 1 for Secretory Cell Lineage Commitment in the Mouse Intestine," Science, 2001, 294:2155.
Ye et al., "Recognition of phosphodegron motifs in human cyclin E by the SCF(Fbw7) ubiquitin ligase," The Journal of biological chemistly, 2004, 279:50110-50119.
Yoneda, "Attempt to regenerate cochlear morphology and function using gene transfer," Otol. Jpn., May 2006, 16(2):135-138 (with machine translation).
Zaragosi et al., "Effects of GSK3 inhibitors on in vitro expansion and differentiation of human adipose-derived stem cells into adipocytes," BMC Cell Biology, 2008, 9: 11.
Zhang et al., "Gene regulatory networks mediating canonical Wnt signal-directed control of pluripotency and differentiation in embryo stem cells," Stem Cells, 2013, 31(12):2667-79.
Zhang et al., "Mule determines the apoptotic response to HDAC inhibitors by targeted ubiquitination and destruction ofHDAC2," Genes & Development, 2011, 25:2610-2618.
Zhao et al., "The HECT-domain ubiquitin ligase Huwe1 controls neural differentiation and proliferation by destabilizing the N-Myc oncoprotein," Nature Cell Biology, 2008, 10:643-653.
Zhao et al., "The N-Myc-DLL3 cascade is suppressed by the ubiquitin ligase Huwe1 to inhibit proliferation and promote neurogenesis in the developing brain," Developmental Cell, 2009, 17:210-221.
Zheng and Gao, "Overexpression of Math1 induces robust production of extra hair cells in postnatal rat inner ears," Nat. Neurosci., 2000, 3:580-586.
Zheng et al., "Induction of Cell Proliferation by Fibroblast and Insulin-Like Growth Factors in Pure Rat Inner Ear Epithelial Cell Cultures," J. Neurosci., 17:216-226 (1997).
Zhong et al., "Mule/ARF-BP1, a BH3-only E3 ubiquitin ligase, catalyzes the polyubiquitination of Mcl-1 and regulates apoptosis," Cell, 2005, 21:1085-1095.

(56) References Cited

OTHER PUBLICATIONS

Zhou et al., "Nuclear GSK3β promotes tumorigenesis by phosphorylating KDMIA and inducing its deubiquitylation by USP22," Nat Cell Biol, Sep. 2016, 18(9):954-966, 28 pages.

Zibetti et al., "Alternative splicing of the histone demethylase LSD1/KDM1 contributes to the modulation of neurite morphogenesis in the mammalian nervous system," J Neurosci, Feb. 2010, 30(7):2521-2532.

Zine et al., "Hes1 and Hes5 activities are required for the normal development of the hair cells in the mammalian inner ear," J Neurosci., 21:4712-20 (Jul. 1, 2001).

Zine et al., "Notch signaling regulates the pattern of auditory hair cell differentiation in mammals," Development., 2000, 127:3373-3383.

Agrup et al., "The inner ear and the neurologist," J Neurol Neurosurg Psychiatry, Feb. 2007, 78(2):114-22.

Mimasu et al., "Structurally designed trans-2-phenylcyclopropylamine derivatives potently inhibit histone demethylase LSD1/KDM1," Biochemistry, Aug. 2010, 49(30):6494-6503.

\* cited by examiner

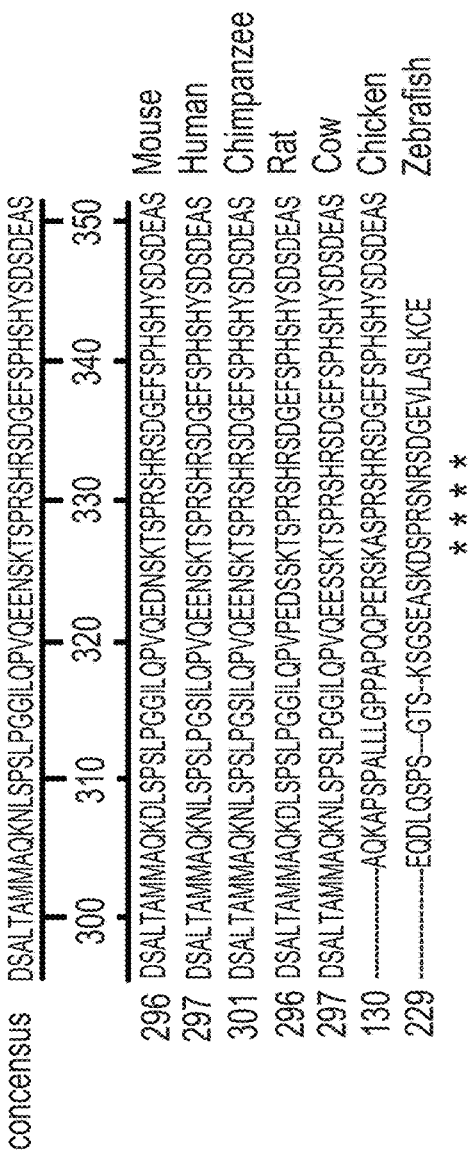
FIG. 5A
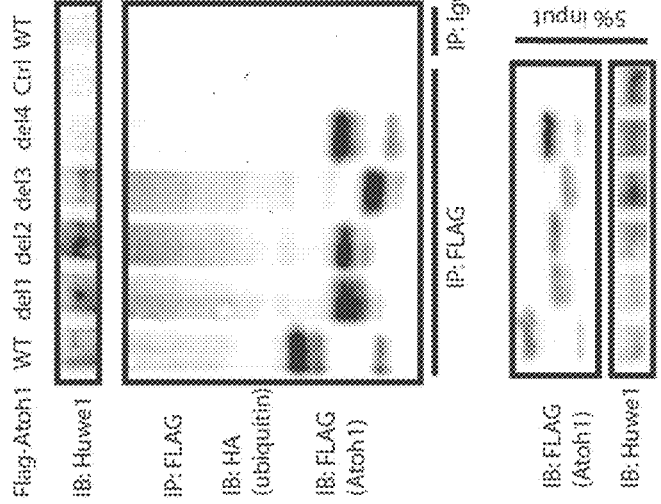
FIG. 4A
FIG. 4B

SEQUENCE LISTING

```
<160> NUMBER OF SEQ ID NOS: 19

<210> SEQ ID NO 1
<211> LENGTH: 20
<212> TYPE: PRT
<213> ORGANISM: Mus musculus

<400> SEQUENCE: 1

Ala Ala Gln Tyr Leu Leu His Ser Pro Glu Leu Gly Ala Ser Glu Ala
1               5                   10                  15

Ala Ala Pro Arg
```

-continued

20

<210> SEQ ID NO 2
<211> LENGTH: 11
<212> TYPE: PRT
<213> ORGANISM: Mus musculus

<400> SEQUENCE: 2

Asp Glu Ala Asp Ser Gln Gly Glu Leu Val Arg
1               5                   10

<210> SEQ ID NO 3
<211> LENGTH: 20
<212> TYPE: PRT
<213> ORGANISM: Mus musculus

<400> SEQUENCE: 3

Asp Leu Ser Pro Ser Leu Pro Gly Gly Ile Leu Gln Pro Val Gln Glu
1               5                   10                  15

Asp Asn Ser Lys
            20

<210> SEQ ID NO 4
<211> LENGTH: 20
<212> TYPE: PRT
<213> ORGANISM: Mus musculus

<400> SEQUENCE: 4

Asp Leu Ser Pro Ser Leu Pro Gly Gly Ile Leu Gln Pro Val Gln Glu
1               5                   10                  15

Asp Asn Ser Lys
            20

<210> SEQ ID NO 5
<211> LENGTH: 24
<212> TYPE: PRT
<213> ORGANISM: Mus musculus

<400> SEQUENCE: 5

Asp Leu Ser Pro Ser Leu Pro Gly Gly Ile Leu Gln Pro Val Gln Glu
1               5                   10                  15

Asp Asn Ser Lys Thr Ser Pro Arg
            20

<210> SEQ ID NO 6
<211> LENGTH: 24
<212> TYPE: PRT
<213> ORGANISM: Mus musculus

<400> SEQUENCE: 6

Asp Leu Ser Pro Ser Leu Pro Gly Gly Ile Leu Gln Pro Val Gln Glu
1               5                   10                  15

Asp Asn Ser Lys Thr Ser Pro Arg
            20

<210> SEQ ID NO 7
<211> LENGTH: 21
<212> TYPE: PRT
<213> ORGANISM: Mus musculus

<400> SEQUENCE: 7

Ser His Arg Ser Asp Gly Glu Phe Ser Pro His Ser His Tyr Ser Asp
1               5                   10                  15

Ser Asp Glu Ala Ser
            20

<210> SEQ ID NO 8
<211> LENGTH: 18
<212> TYPE: PRT
<213> ORGANISM: Mus musculus

<400> SEQUENCE: 8

Ser Asp Gly Glu Phe Ser Pro His Ser His Tyr Ser Asp Ser Asp Glu
1               5                   10                  15

Ala Ser

<210> SEQ ID NO 9
<211> LENGTH: 18
<212> TYPE: PRT
<213> ORGANISM: Mus musculus

<400> SEQUENCE: 9

Ser Asp Gly Glu Phe Ser Pro His Ser His Tyr Ser Asp Ser Asp Glu
1               5                   10                  15

Ala Ser

<210> SEQ ID NO 10
<211> LENGTH: 18
<212> TYPE: PRT
<213> ORGANISM: Mus musculus

<400> SEQUENCE: 10

Ser Asp Gly Glu Phe Ser Pro His Ser His Tyr Ser Asp Ser Asp Glu
1               5                   10                  15

Ala Ser

<210> SEQ ID NO 11
<211> LENGTH: 18
<212> TYPE: PRT
<213> ORGANISM: Mus musculus

<400> SEQUENCE: 11

Ser Asp Gly Glu Phe Ser Pro His Ser His Tyr Ser Asp Ser Asp Glu
1               5                   10                  15

Ala Ser

<210> SEQ ID NO 12
<211> LENGTH: 56
<212> TYPE: PRT
<213> ORGANISM: Artificial Sequence
<220> FEATURE:
<223> OTHER INFORMATION: Atoh-1 N terminus consensus sequence

<400> SEQUENCE: 12

Asp Ser Ala Leu Thr Ala Met Met Ala Gln Lys Asn Leu Ser Pro Ser
1               5                   10                  15

Leu Pro Gly Gly Ile Leu Gln Pro Val Gln Glu Glu Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

```
<210> SEQ ID NO 13
<211> LENGTH: 56
<212> TYPE: PRT
<213> ORGANISM: Mus musculus

<400> SEQUENCE: 13

Asp Arg Ala Leu Thr Ala Met Met Ala Gln Lys Asp Leu Ser Pro Ser
1               5                   10                  15

Leu Pro Gly Gly Ile Leu Gln Pro Val Gln Glu Asp Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 14
<211> LENGTH: 56
<212> TYPE: PRT
<213> ORGANISM: Homo sapiens

<400> SEQUENCE: 14

Asp Ser Ala Leu Thr Ala Met Met Ala Gln Lys Asn Leu Ser Pro Ser
1               5                   10                  15

Leu Pro Gly Ser Ile Leu Gln Pro Val Gln Glu Glu Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 15
<211> LENGTH: 56
<212> TYPE: PRT
<213> ORGANISM: Pan troglodytes

<400> SEQUENCE: 15

Asp Ser Ala Leu Thr Ala Met Met Ala Gln Lys Asn Leu Ser Pro Ser
1               5                   10                  15

Leu Pro Gly Ser Ile Leu Gln Pro Val Gln Glu Glu Asn Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 16
<211> LENGTH: 56
<212> TYPE: PRT
<213> ORGANISM: Rattus norvegicus

<400> SEQUENCE: 16

Asp Arg Ala Leu Thr Ala Met Met Ala Gln Lys Asp Leu Ser Pro Ser
1               5                   10                  15

Leu Pro Gly Gly Ile Leu Gln Pro Val Pro Glu Asp Ser Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55
```

```
<210> SEQ ID NO 17
<211> LENGTH: 56
<212> TYPE: PRT
<213> ORGANISM: Bos taurus

<400> SEQUENCE: 17

Asp Ser Ala Leu Thr Ala Met Met Ala Gln Lys Asn Leu Ser Pro Ser
1               5                   10                  15

Leu Pro Gly Gly Ile Leu Gln Pro Val Gln Glu Glu Ser Ser Lys Thr
            20                  25                  30

Ser Pro Arg Ser His Arg Ser Asp Gly Glu Phe Ser Pro His Ser His
        35                  40                  45

Tyr Ser Asp Ser Asp Glu Ala Ser
    50                  55

<210> SEQ ID NO 18
<211> LENGTH: 48
<212> TYPE: PRT
<213> ORGANISM: Gallus gallus

<400> SEQUENCE: 18

Ala Gln Lys Ala Pro Ser Pro Ala Leu Leu Leu Gly Pro Pro Ala Pro
1               5                   10                  15

Gln Gln Pro Glu Arg Ser Lys Ala Ser Pro Arg Ser His Arg Ser Asp
            20                  25                  30

Gly Glu Phe Ser Pro Arg Ser His Tyr Ser Asp Ser Asp Glu Ala Ser
        35                  40                  45

<210> SEQ ID NO 19
<211> LENGTH: 38
<212> TYPE: PRT
<213> ORGANISM: Danio rerio

<400> SEQUENCE: 19

Glu Gln Asp Leu Gln Ser Pro Ser Gly Thr Ser Lys Ser Gly Ser Glu
1               5                   10                  15

Ala Ser Lys Asp Ser Pro Arg Ser Asn Arg Ser Asp Gly Glu Val Leu
            20                  25                  30

Ala Ser Leu Lys Cys Glu
        35
```

TREATMENT OF HEARING LOSS BY INHIBITION OF CASEIN KINASE 1

CLAIM OF PRIORITY

This application is a divisional of U.S. patent application Ser. No. 15/781,041, filed on Jun. 1, 2018, which is a 371 U.S. National Phase Application of PCT/US2016/064727, filed on Dec. 2, 2016, which claims the benefit of U.S. Provisional Patent Application Ser. No. 62/263,412, filed on Dec. 4, 2015. The entire contents of the foregoing are hereby incorporated by reference herein.

FEDERALLY SPONSORED RESEARCH OR DEVELOPMENT

This invention was made with Government support under Grant No. RO1 DC007174 awarded by the National Institutes of Health. The Government has certain rights in the invention.

SEQUENCE LISTING

This application contains a Sequence Listing that has been submitted electronically as an ASCII text file named "Sequence_Listing.txt." The ASCII text file, created on Oct. 8, 2021, is 8 KB in size. The material in the ASCII text file is hereby incorporated by reference in its entirety.

TECHNICAL FIELD

Described herein are methods for treating hearing loss that include administering an inhibitor, e.g., a small molecule inhibitor, of casein kinase 1, preferably in combination with a treatment that stimulates Atoh1 gene expression, e.g., a gamma-secretase inhibitor, an Atoh1 stimulatory compound, or a GSK-3-beta inhibitor.

BACKGROUND

Loss of mammalian cochlear hair cells, caused by genetic mutations, autoimmune disease, ototoxic medications, exposure to noise, and aging, is usually permanent and can lead to mild to complete hearing loss in affected subjects.

SUMMARY

The present disclosure provides, inter alia, methods and pharmaceutical compositions for treating subjects for the conditions described herein. Accordingly, the present disclosure is based, at least in part, on the discovery that differentiation of a cell to or towards a mature cell of the inner ear, e.g., an auditory hair cell can be promoted through β-catenin-dependent WNT signaling. In other words, the present disclosure provides methods and compositions relating to the WNT/β-catenin signaling pathway for generating cells that have characteristics of auditory hair cells.

Thus, the present disclosure provides methods for treating a subject who has or is at risk of developing hearing loss or vestibular dysfunction. The methods can include identifying a subject who has experienced, or is at risk for developing, hearing loss or vestibular dysfunction; administering to the subject, e.g., to the ear of the subject one or more one or more casein kinase 1 (CK1) inhibitors, and optionally one or more compounds that stimulate Atoh1 gene expression, e.g., a gamma-secretase inhibitor, an Atoh1 stimulatory compound, or a GSK-3-beta inhibitor, thereby treating the hearing loss or vestibular dysfunction in the subject. Also provided herein are a casein kinase 1 (CK1) inhibitor, and optionally a compound that stimulates Atoh1 gene expression, for use in treating a subject who has or is at risk of developing hearing loss or vestibular dysfunction.

In some embodiments, the subject has or is at risk for developing sensorineural hearing loss, auditory neuropathy, or both.

In some embodiments, the subject has or is at risk for developing a vestibular dysfunction that results in dizziness, imbalance, or vertigo.

In some embodiments, the casein kinase 1 (CK1) inhibitors and/or the one or more compounds that stimulate Atoh1 gene expression is administered systemically. In some embodiments, the casein kinase 1 (CK1) inhibitors and/or the one or more compounds that stimulate Atoh1 gene expression is administered locally to the ear of the subject, e.g., to the inner ear. In some embodiments, the one or more compounds that stimulate Atoh1 gene expression comprises one or more glycogen synthase kinase 3 β (GSK3β) inhibitors. In some embodiments, the one or more small molecule casein kinase 1 (CK1) inhibitor is D4476. In some embodiments, the one or more compounds that stimulate Atoh1 gene expression is a gamma secretase inhibitor. In some embodiments, a combination of CHIR99021 and LY411575 is used.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

HEK cells were co-transfected with HA-ubiquitin and FLAG-Atoh1 plasmids for 48 hours and treated with CK1 inhibitors (PF-670462 or D4476) and/or proteasome inhibitor MG132 (10 μM) for 4 hours. Immunoprecipitation was performed under denaturing conditions with anti-FLAG antibody. Endogenous Huwe1 was detected with an anti-Huwe1 antibody. Atoh1 was detected with anti-FLAG while ubiquitin was detected with anti-HA antibodies.

Figure 3A:
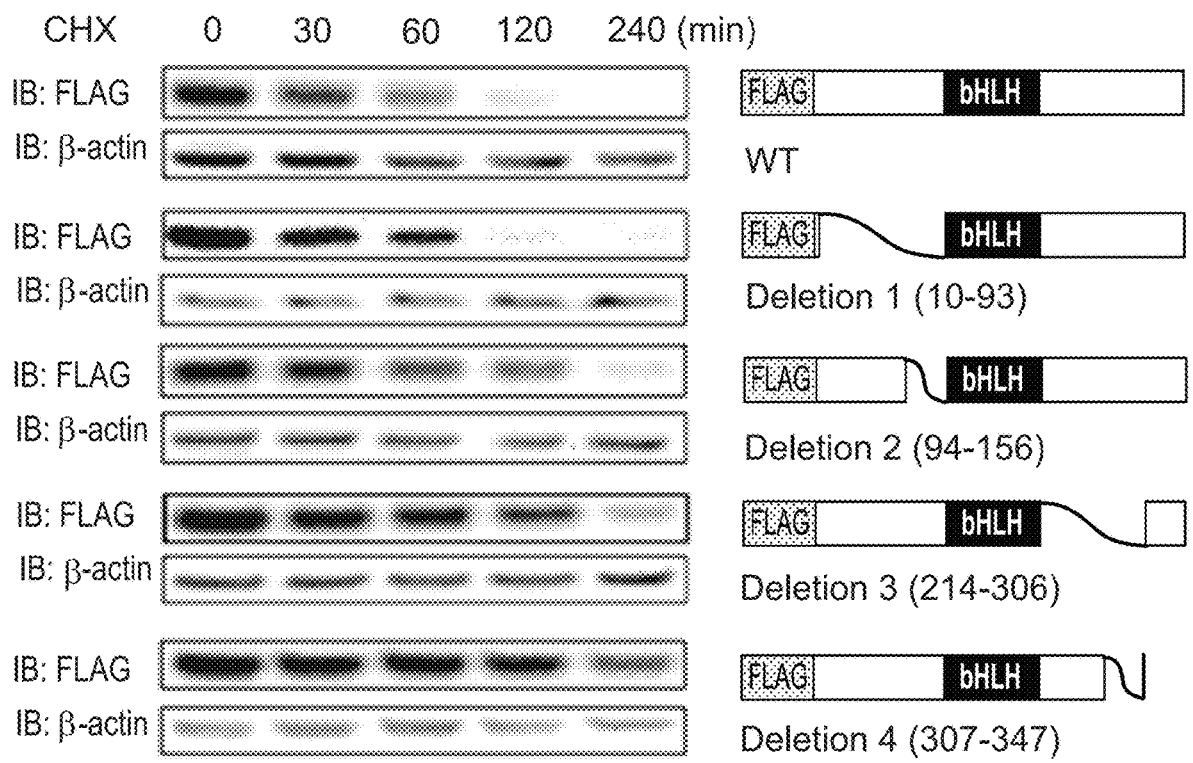
Figure 3B:
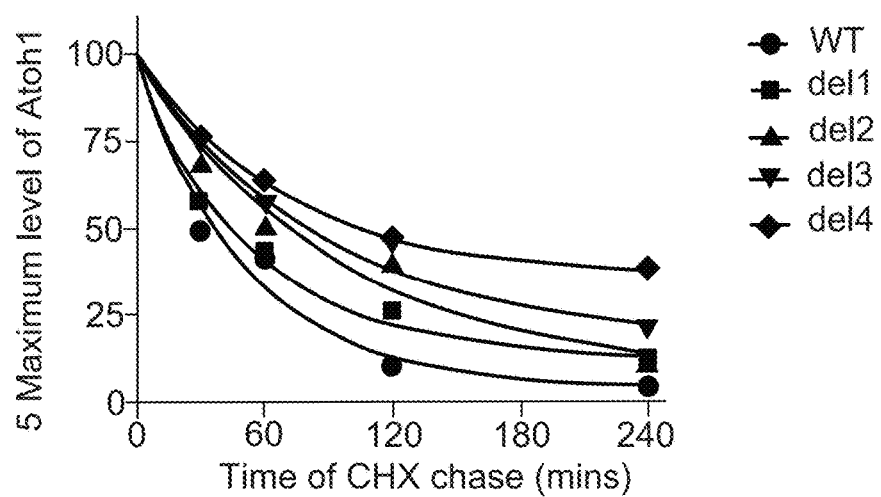

FIGS. 3A-B. Evolutionarily conserved serines in the C-terminus of Atoh1 account for its stability (A) Half-life analysis of truncated Atoh1 over a 4-hour time frame. HEK cells were transfected with either wild-type or truncated FLAG Atoh1 for 48 hours and incubated with cycloheximide (100 μg/ml) for the indicated times. β-actin served as a loading control for input protein.

(B) Quantification of protein half-lives. The ratio of Atoh1 to β-actin based on densitometry was plotted.

FIGS. 4A-B. A signal for Huwe1 binding is located in the C-terminus of Atoh1

(A) Truncation of Atoh1 influences Huwe1 interaction. HEK cells were co-transfected with HA-ubiquitin and wild-type or truncated FLAG Atoh1 plasmids (Δ10-93 for deletion 1, Δ94-156 for deletion 2, Δ214-305 for deletion 3 and Δ306-347 for deletion 4) for 48 hours. Immunoprecipitation was performed under denaturing conditions with anti-FLAG antibody. Atoh1 was detected with the anti-HA and anti-FLAG antibodies. Endogenous Huwe1 was detected with an anti-Huwe1 antibody. Immunoprecipitation with IgG was used for the control.

(B) Blotting of endogenous Huwe1 and Atoh1. Five percent of total extracts from the experiment shown in A were analyzed by Western blotting with an anti-FLAG antibody to detect Atoh1 and anti-Huwe1 to detect endogenous Huwe1.

Figure 5B:
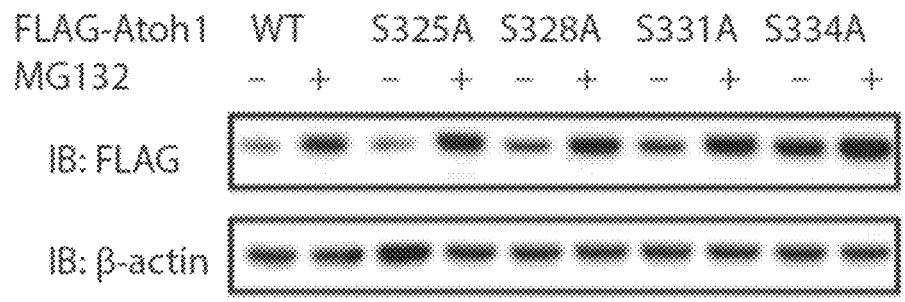
Figure 5C:
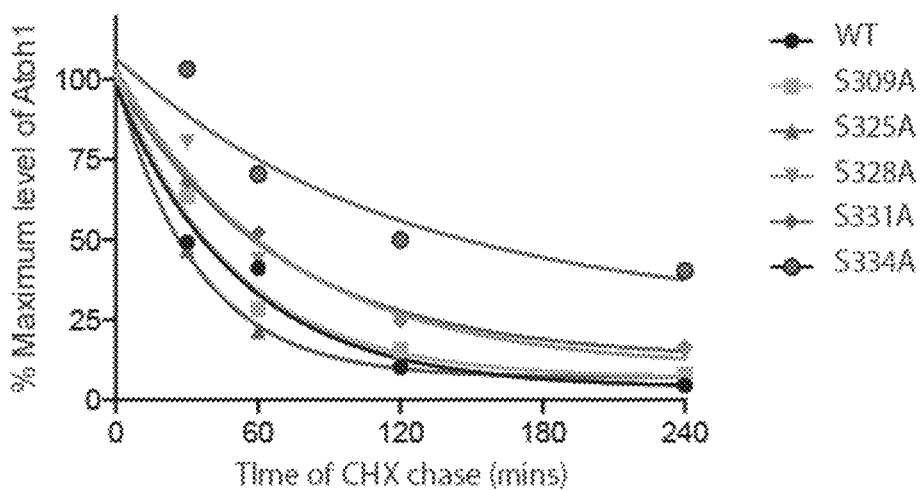

FIGS. 5A-C. Serine 334 is a critical residue for Atoh1 degradation (A) C-terminal regions of Atoh1 (area 4) of different species were aligned. Conserved serines at 325, 328, 331 and 334 are marked with asterisks. The corresponding residues in the human sequence are 328, 331, 334 and 337. The sequences shown are SEQ ID NOs:12-19 in order, respectively.

(B) Serine to alanine mutations affects the steady-state level of Atoh1. HEK cells were transfected with wild-type or mutated FLAG Atoh1 plasmids for 40 hours and treated with either vehicle (DMSO) or MG132 (10 μM). After treatment with proteasome inhibitor for 6 hours, S334A had the smallest increase in Atoh1 (vehicle treatment is marked with a minus sign) compared to wild-type or other Atoh1 mutants.

(C) Half-life analysis of mutated Atoh1 proteins over a 4-hour time frame. HEK cells were transfected with either wild-type or mutated FLAG Atoh1 plasmids for 40 hours and incubated with cycloheximide (100 μg/ml) for the indicated times. The ratio of Atoh1 to β-actin based on densitometry was plotted.

Figure 6:
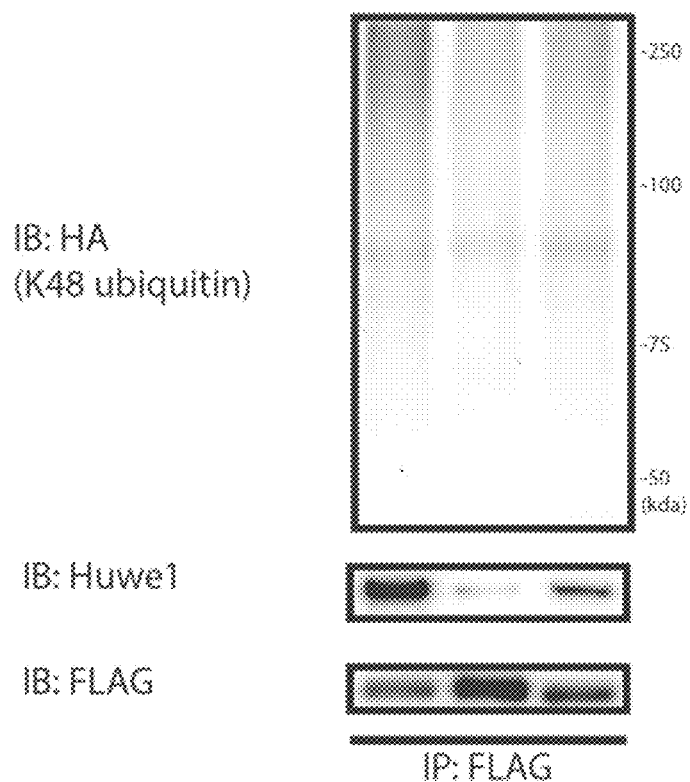

FIG. 6. Mutation at Serine 334 of Atoh1 decreases Huwe1 binding and ubiquitylation Mutation of Atoh1 influences Huwe1 interaction. HEK cells were co-transfected with ubiquitin with all lysines except K48 mutated and wild type or mutated FLAG Atoh1 plasmids (S334A or S328/329A) for 48 hours. Immunoprecipitation was performed under denaturing conditions with an anti-FLAG antibody. Endogenous Huwe1 was detected with an anti-Huwe1 antibody. Atoh1 was detected with an anti-FLAG antibody while ubiquitin was detected with an anti-HA antibody.

Figure 7A:
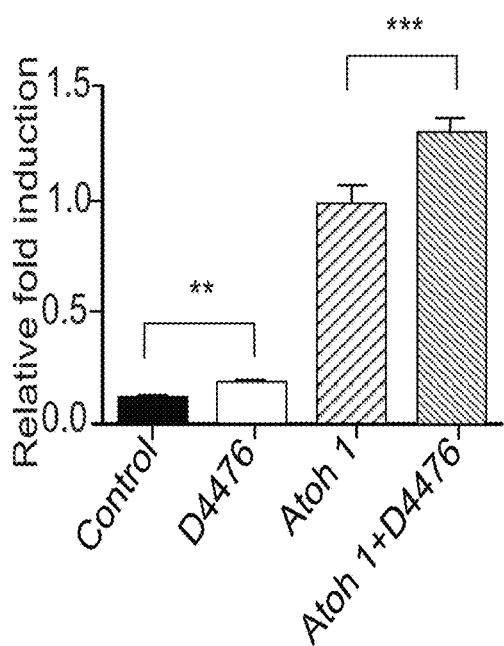
Figure 7B:
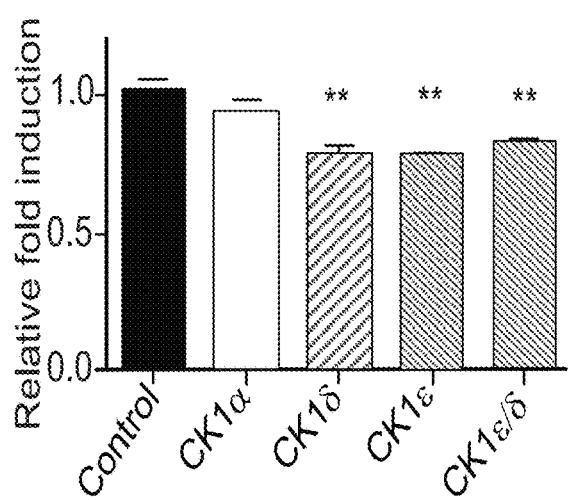
Figure 7C:
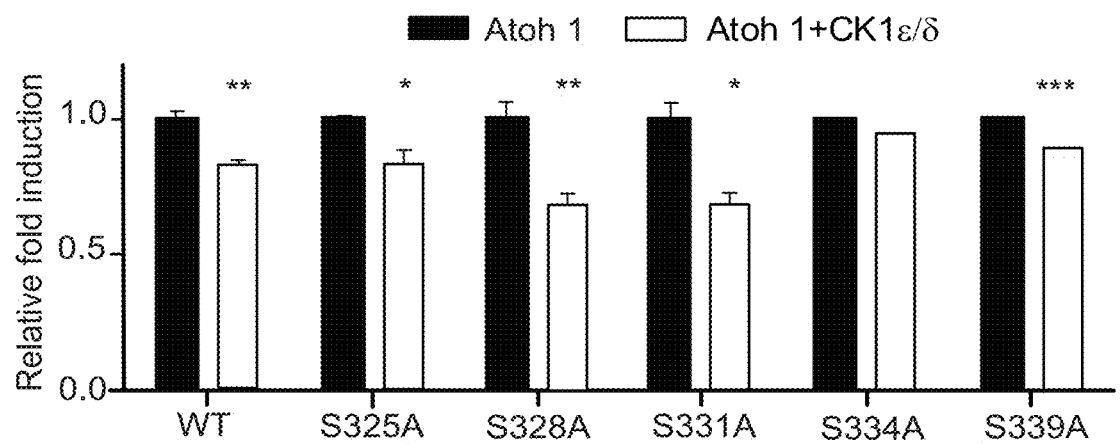

FIGS. 7A-C. S334 is essential for CK1-mediated Atoh1 downstream signaling

Dual luciferase assay using a firefly reporter construct with an AtEAM motif in HEK cells. Experiments were done in triplicate, and data are presented as the mean±SEM after normalization to *Renilla* luciferase (A) CK1 inhibition (D4476) increases Atoh1-specific E-box activity. DMSO or CK1 inhibitor D4476 was added to HEK with or without overexpression of Atoh1 for overnight to block the degradation of Atoh1 and therefore downstream Atoh1-specific E-box activity.

(B) CK1δ and/or CK1ε reduce Atoh1-specific E-box activity. Overexpression of CK1δ and/or CK1ε in HEK cells co-transfected with Atoh1 plasmid significantly reduce Atoh1-specific E-box activity. The effect of CK1 isoform, CK1a, was not significant (C) S334 is essential for CK1-mediated reduction of Atoh1-specific E-box activity. HEK cells were co-transfected with CK1δ & CK1ε (CK1ε/δ) and wild-type or mutated Atoh1 plasmids. CK1-mediated reduction of Atoh1-specific E-box activity was abolished when S334 residue was mutated to alanine (S334A). Such CK1-mediated reduction was seen for other mutated residues, including S325A, S328A, S331A and S339A.

Figure 8:
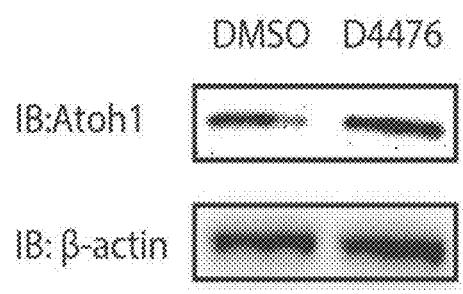

FIG. 8. CK1 inhibition stabilizes Atoh1 protein in the organ of Corti.

Effect of CK1 inhibition on Atoh1 upregulation in the organ of Corti. Newborn organs of Corti (P1) were treated with the CK1 inhibitor D4476 (10 uM) for 72 hours. Atoh1 were quantified after Western blotting by densitometry and normalized to a loading control (beta-actin).

Figure 9A:
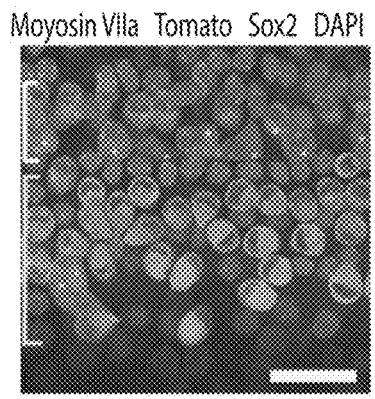
Figure 9B:
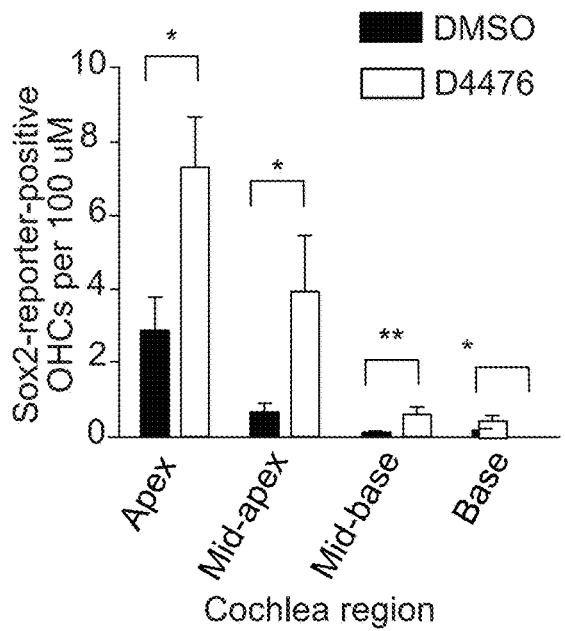
Figure 9C:
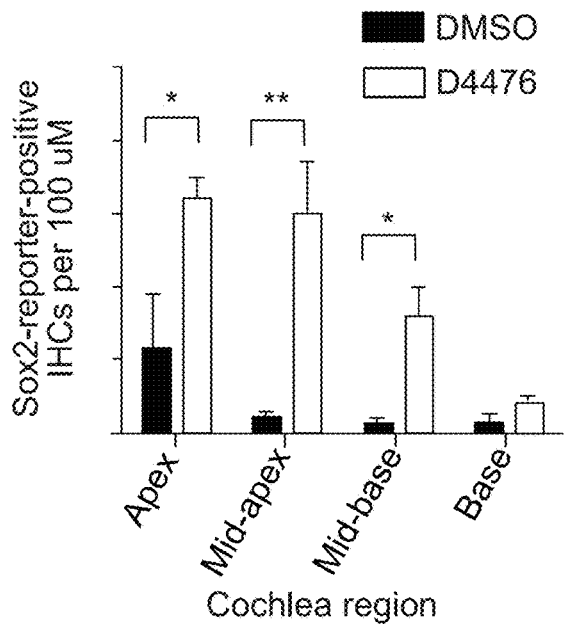

FIGS. 9A-C. Sox2 Lineage Tracing of Supporting Cells in Neonatal Cochleae Treated with Ck1 inhibitor D4476.

(A) Double-labeled cells positive for Sox2 lineage (tomato) and myosin VIIa (green) were found both in the inner hair cell and outer hair cell area in the mid-base region of cochlear tissue from neonatal mice carrying the Sox2-CreER as well as the Cre reporter 3 days after treatment with CK1 inhibitor D4476 (10 nM). Hair cell co-labeling with the lineage tag indicates derivation from a Sox2-positive cell (labeled with asterisks) and is thus evidence for newly generated hair cells by transdifferentiation of supporting cells. OHCs, at the bottom of the image, are delineated by a light gray bracket while IHCs, at the top of the image, are delineated by a white bracket. The scale bar is 25 μm.

(B, C) Effect of CK1 inhibition was significant. Quantification of the reporter-positive OHC and IHC counts for Sox2 lineage tracing of DMSO and D4476 treated explants showed significantly more reporter-labeled OHCs (B) and IHCs (C) across most cochlear regions after D4476 treatment (mean±SEM per 100 mm, plotted on a logarithmic scale; *$p<0.05$, **$p<0.01$, n=4-8 for both groups).

Figure 10:
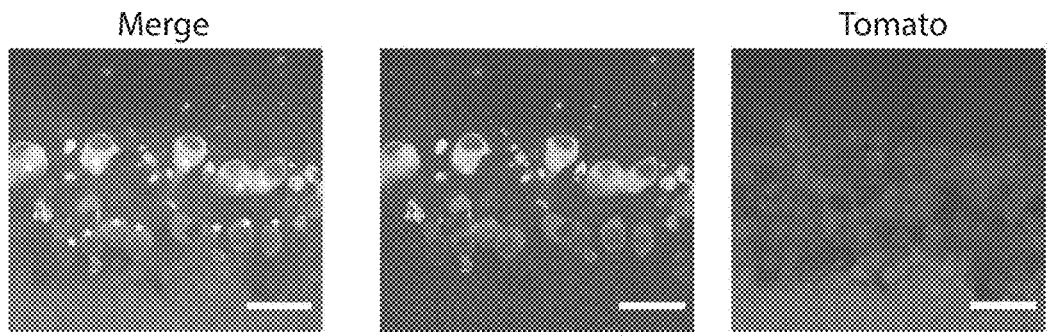

FIG. 10. Transdifferentiation of Sox2-positive supporting cell into hair cells results from CK1 inhibition after aminoglycoside damage.

Images of the basal turn of the lineage-traced organ of Corti damaged by gentamycin and treated with CK1 inhibitor D4476 for 72 hours. Doubled-labeled cells positive for Sox2 lineage (tomato in original image) and myosin VIIa (green in original image), marked with an asterisk in the leftmost panel, indicated transdifferentiation of supporting cells. The scale bar is 25 μm.

DETAILED DESCRIPTION

Mammals show limited ability to regenerate hair cells (Forge et al., Science 259, 1616-1619 (1993); Warchol et al., Science 259, 1619-1622 (1993)). Hair cell differentiation is dependent on basic helix-loop-helix (bHLH) transcription factor, Atoh1. Overexpression of Atoh1 via gene transfer results in the generation of new hair cells from inner ear progenitors in the organ of Corti (Bermingham et al., Science 284, 1837-1841 (1999); Jeon et al., Mol Cell Neurosci 34, 59-68 (2007)). Several regulatory pathways have been found to be involved in Atoh1 regulation (Zhang et al., Stem Cells 31(12):2667-79 (2013); Jeon et al., J. Neurosci. 31, 8351-8358 (2011); Kelley et al., Nat Rev Neurosci 7, 837-849 (2006); Shi et al., J Biol Chem 285, 392-400 (2010)). The present inventors have discovered that post-translationally, levels of Atoh1 are controlled at least in part by ubiquitylation by Huwe1, a HECT-domain, E3 ubiquitin ligase, which targets Atoh1 for proteasomal degradation by polyubiquitylation (see Cheng, "Role of the ubiquitin-proteasome pathway in the inner ear: identification of an E3 ubiquitin ligase for Atoh1," Thesis: Ph. D., Harvard-MIT Program in Health Sciences and Technology, 2014, available online at hdl.handle.net/1721.1/96458; and PCT/US2015/043976).

In addition to E3 ubiquitin ligase, specification of a substrate for ubiquitylation and degradation also comes from post-translational modification of degrons (a sequence within a protein that is sufficient for recognition and degradation by a proteolytic apparatus), which allows substrate ubiquitylation in response to endogenous or external signals (Ravid and Hochstrasser, Nat Rev Mol Cell Biol. 9(9):679-90 (2008)). We found that the serine-enriched C-terminus of Atoh1 had a number of evolutionarily conserved serines at positions 309, 325, 328, 331 and 334, and putative motifs for phosphorylation by casein kinase 1 (CK1), pSer/Thr-X-XSer/Thr, starting from Ser 325, followed by Ser 328, 331 and 334. CK1 is a serine/threonine protein kinase that triggers phosphorylation of substrates, and has Ck1α, CK1δ, CK1ε and CK1γ isoforms. Since CK1 isoforms have molecular weight ranging from 32 to 52.5 kDa (Knippschild et al., 2014), which are close to Atoh1, we conducted mass spectrometry on the band at 45 kDa from lysates immunoprecipitated with Atoh1 (Table I). CK1ε and CK1γ were identified in the proteins at this molecular weight. Small molecule CK1 inhibitors, including D4476 (4-[4-(2,3-Dihydro-1,4-benzodioxin-6-yl)-5-(2-pyridinyl)-1H-imidazol-2-yl]benzamide), IC-261 (1,3-Dihydro-3-[(2,4,6-trimethoxyphenyl)methylene]-2H-indol-2-one, also known as SU5607), and PF-670462 (4-[3-Cyclohexyl-5-(4-fluorophenyl)-3H-imidazol-4-yl]-pyrimidin-2-ylamine dihydrochloride) increased the steady-state abundance of Atoh1 in human 293T cells; D4476 was also shown to increase hair cell generation in the organ of Corti and promote hair cell regeneration after aminoglycoside damage.

In some embodiments, the present methods include using a CK1 inhibitor, e.g., a small molecule CK1 inhibitor, which increases the half-life and thus the overall amount of Atoh1 protein, is administered in combination with a treatment that stimulates Atoh1 gene expression, e.g., a gamma-secretase inhibitor, an Atoh1 stimulatory compound, or a GSK-3-beta inhibitor.

Casein Kinase Inhibitors

Casein Kinase 1 inhibitors include, e.g., PF 670462 (4-[1-Cyclohexyl-4-(4-fluorophenyl)-1H-imidazol-5-yl]-2-pyrimidinamine dihydrochloride) (Sigma); IC261 (3-[(2,4,6 trimethoxyphenyl)methylidenyl]-indolin-2-one (Abcam); D 4476 (4-[4-(2,3-Dihydro-1,4-benzodioxin-6-yl)-5-(2-pyridinyl)-1H-imidazol-2-yl]benzamide (R &D Systems); LH 846 (N-(5-Chloro-6-methyl-2-benzothiazolyl)benzeneacetamide) (Tocris Bioscience); 6-cycloamino-3-(pyrid-4-yl) imidazo[1,2-b]pyridazine derivatives (Sanofi Aventis), see US20100179154. Casein Kinase 1 selective inhibitors also include the following: 4-((6-methoxy-3-pyridinyl)methylene)-2-(5-fluoro-2-thienyl)-5(4H)-oxazolone; 4-((6-methoxy-3 pyridinyl)methylene)-2-(5-chloro-2-thienyl)-5 (4H)-oxazolone; 4-((6-methoxy-3-pyridinyl)methylene)-2-(5-bromo-2-thienyl)-5(4H)-oxazolone; 4-((6-methoxy-3-pyridinyl)methylene)-2-(5-iodo-2-thienyl)-5(4H)-oxazolone (Pfizer), see U.S. Pat. No. 8,518,944; PF-4800567 (3-[(3-Chlorophenoxy)methyl]-1-(tetrahydro-2H-pyran-4-yl)-1H-pyrazolo[3,4-d]pyrimidin-4-amine hydrochloride) (Calbiochem); 4-[4-(4-Fluorophenyl)-5-(2-pyridyl)-1-hydroxy-1H-imidazol-2-yl]benzonitrile and derivatives (Roche), see US20090099237.

In some embodiments, suitable kinase inhibitors can include inhibitory nucleic acids, e.g., shRNA or siRNA, that target CK1 and decrease CK1 protein levels. In some embodiments, suitable kinase inhibitors does not include inhibitory nucleic acids that target CK1 and decrease CK1 protein levels.

Gamma-Secretase Inhibitors

Gamma secretase inhibitors useful in the present methods include, e.g., RO4929097; DAPT (N-[(3,5-Difluorophenyl)acetyl]-L-alanyl-2-phenyl]glycine-1,1-dimethylethyl ester); L-685458 ((5S)-(t-Butoxycarbonylamino)-6-phenyl-(4R) hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); MK-0752; YO-01027; MDL28170 (Sigma); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide, see U.S. Pat. No. 6,541,466); ELN-46719 (2-hydroxy-valeric acid amide analog of LY411575 (where LY411575 is the 3,5-difluoro-mandelic acid amide) (U.S. Pat. No. 6,541,466)); PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide; Samon et al., Mol Cancer Ther 2012; 11:1565-1575); and Compound E ((2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide; see WO 98/28268 and Samon et al., Mol Cancer Ther 2012; 11:1565-1575; available from Alexis Biochemicals)), or pharmaceutically acceptable salts thereof.

In some embodiments, suitable gamma secretase inhibitors include: semagacestat (also known as LY450139, (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]butanamide, available from Eli Lilly; WO 02/47671 and U.S. Pat. No. 7,468,365); LY411575 (N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-L-alaninamide, available from Eli Lilly, Fauq et al., Bioorg Med Chem Lett 17: 6392-5, 2007); begacestat (also known as GSI-953, U.S. Pat. No. 7,300,951); arylsulfonamides (A S, Fuwa et al., Bioorg Med Chem Lett. 16(16):4184-4189, 2006); N—[N-(3,5-difluorophenacetyl)-L-alanyl]-(S)-phenylglycine t-butyl ester (DAPT, Shih and Wang, Cancer Res. 67: 1879-1882, 2007); N—[N-3,5-Difluorophenacetyl]-L-alanyl-S-phenylglycine Methyl Ester (also known as DAPM, gamma-Secretase Inhibitor XVI, available from EMD Millipore); Compound W (3,5-bis(4-Nitrophenoxy) benzoic acid, available from Tocris Bioscience); L-685,458 ((5S)-(tert-Butoxycarbonylamino)-6-phenyl-(4R)-hydroxy-(2R)-benzylhexanoyl)-L-leucy-L-phenylalaninamide, available from Sigma-Aldrich, Shearmen et al., Biochemistry 39, 8698-8704, 2000); BMS-289948 (4-chloro-N-(2,5-difluorophenyl)-N-((1R)-{4-fluoro-2-[3-(1H-imidazol-1-yl)propyl] phenyl}ethyl)benzenesulfonamide hydrochloride, available from Bristol Myers Squibb); BMS-299897 (4-[2-((1R)-1-{[(4-chlorophenyl)sulfonyl]-2,5-difluoroanilino}ethyl)-5-fluorophenyl]butanoic acid, available from Bristol Myers Squibb, see Zheng et al., Xenobiotica 39(7):544-55, 2009); avagacestat (also known as BMS-708163, (R)-2-(4-chloro-N-(2-fluoro-4-(1,2,4-oxadiazol-3-yl)benzyl)phenylsulfonamido)-5,5,5-trifluoropentanamide, available from Bristol Myers Squibb, Albright et al., J Pharmacol. Exp. Ther. 344(3):686-695, 2013); MK-0752 (3-(4-((4-chlorophenyl)

sulfonyl)-4-(2,5-difluorophenyl)cyclohexyl)propanoic acid, available from Merck); MRK-003 ((3'R,6R,9R)-5'-(2,2,2-trifluoroethyl)-2-((E)-3-(4-(trifluoromethyl)piperidin-1-yl) prop-1-en-1-yl)-5,6,7,8,9,10-hexahydrospiro[6,9-methanobenzo[8]annulene-11,3'-[1,2,5]thiadiazolidine]1',1'-dioxide, available from Merck, Mizuma et al., Mol Cancer Ther. 11(9):1999-2009, 2012); MRK-560 (N-[cis-4-[(4-Chlorophenyl)sulfonyl]-4-(2,5-difluorophenyl)cyclohexyl]-1,1,1-trifluoro-methanesulfonamide, Best et. al., J Pharmacol Exp Ther. 317(2):786-90, 2006); RO-4929097 (also known as R4733, (S)-2,2-dimethyl-N1-(6-oxo-6,7-dihydro-5H-dibenzo[b,d]azepin-7-yl)-N3-(2,2,3,3,3-pentafluoropropyl) malonamide, available from Hoffman-La Roche Inc., Tolcher et al., J Clin. Oncol. 30(19):2348-2353, 2012); JLK6 (also known as 7-Amino-4-chloro-3-methoxyisocoumarin, available from Santa Cruz Biotechnology, Inc., Petit et al., Nat. Cell. Biol. 3: 507-511, 2001); Tarenflurbil (also known as (R)-Flurbiprofen, (2R)-2-(3-fluoro-4-phenylphenyl)propanoic acid); ALX-260-127 (also known as Compound 11, described by Wolfe et al., J. Med. Chem. 41: 6, 1998); Sulindac sulfide (SSide, Takahashi et al., J Biol Chem. 278(20): 18664-70, 2003); 1,1,1-trifluoro-N-(4-[5-fluoro-2-(trifluoromethyl)phenyl]-4-{[4(trifluoromethyl)phenyl]sulfonyl}cyclohexyl)methanesulfonamide (described in US20110275719); N-[trans-3-[(4-chlorophenyl)sulfonyl]-3-(2,5-difluorophenyl)cyclobutyl]-1,1,1-trifluoromethanesulfonamide (described in US20110263580); N-[cis-3-[(4-chlorophenyl)sulfonyl]-3-(2,5-difluorophenyl)cyclobutyl]-1,1,1-trifluoromethanesulfonamide (described in US20110263580); N-[cis-3-[(4-chlorophenyl)sulfonyl]-3-(2-cyano-5-fluorophenyl)cyclobutyl]-1,1,1-trifluoromethanesulfonamide (described in US20110263580); N-[cis-3-[(4-chlorophenyl)sulfonyl]-3-(2,5-dichlorophenyl) cyclobutyl]-1,1,1-trifluoromethanesulfonamide (described in US20110263580); N-(cis-3-(2,5-difluorophenyl)-3-{[4-(trifluoromethyl)phenyl]sulfonyl}cyclobutyl)-1,1,1-trifluoromethanesulfonamide (described in US20110263580); N-{cis-3-(5-chloro-2-fluorophenyl)-3-[(4-chlorophenyl)sulfonyl]cyclobutyl}-1,1,1-trifluoromethanesulfonamide (described in US20110263580); N-{cis-3-(2,5-difluorophenyl)-3-[(4-fluorophenyl)sulfonyl]cyclobutyl}-1,1,1-trifluoromethanesulfonamide (described in US20110263580); N-{cis-3-(2,5-difluorophenyl)-3-[(3,4-difluorophenyl)sulfonyl]cyclobutyl}-1,1,1-trifluoromethanesulfonamide (described in US20110263580); N-[cis-3-[(4-cyanophenyl)sulfonyl]-3-(2,5-difluorophenyl)cyclobutyl]-1,1,1-trifluoromethanesulfonamide (described in US20110263580); 4-{[cis-3-[(4-chlorophenyl)sulfonyl]3-(2,5-difluorophenyl)cyclobutyl][trifluoromethyl) sulfonyl]amino}butanoic acid (described in US20110263580); N-[cis-3-[(4-chlorophenyl)sulfonyl]-3-(2,5-difluorophenyl)cyclobutyl]-1,1,1-trifluoro-N-[2-(tetrahydro-2-pyran-2-yloxy)ethyl]methanesulfonamide (described in US20110263580); Methyl{[cis-3-[(4-chlorophenyl)sulfonyl]-3-(2,5-difluorophenyl)cyclobutyl][(trifluoromethyl)sulfonyl]amino}acetate (described in US20110263580); N-[3-[(4-chlorophenyl)sulfonyl]-3-(2,5-difluorophenyl)cyclobutyl]-1,1,1-trifluoro-N-methylmethanesulfonamide (described in US20110263580); N-[3-[(4-chlorophenyl)sulfonyl]-3-(2,5-difluorophenyl)cyclobutyl]-1,1,1-trifluoro-N-methylmethanesulfonamide (described in US20110263580); Methyl 4-{[cis-3-[(4-chlorophenyl)sulfonyl]-3-(2,5-difluorophenyl)cyclobutyl][(trifluoro-methyl) sulfonyl]amino}butanoate (described in US20110263580); N-[cis-3-[(4-chlorophenyl)sulfonyl]-3-(2,5-difluorophenyl)cyclobutyl]-N-[(trifluoromethyl)sulfonyl]glycine (described in US20110263580); N-[cis-3-[(4-chlorophenyl)sulfonyl]-3-(2,5-difluorophenyl)-1-methylcyclobutyl]-1,1,1-trifluoromethanesulfonamide (described in US20110263580); N-(cis-3-(2,5-difluorophenyl)-1-methyl-3-{[4-(trifluoromethyl)phenyl]sulfonyl}cyclobutyl)-1,1,1-trifluoromethanesulfonamide (described in US20110263580); N-[cis-3-[(4-chlorophenyl)sulfonyl]-3-(2,5-difluorophenyl)cyclobutyl]-1,1,1-trifluoro-N-[(trifluoromethyl)sulfonyl] methanesulfonamide (described in US20110263580); Sodium[cis-3-[(4-chlorophenyl)sulfonyl]-3-(2,5-difluorophenyl)cyclobutyl][(trifluoromethyl)sulfonyl]azanide (described in US20110263580); Potassium[cis-3-[(4-chlorophenyl)sulfonyl]-3-(2,5-difluorophenyl)cyclo butyl][(trifluoromethyl)sulfonyl]azanide (described in US20110263580); N-[cis-3-[(4-trifluoromethoxyphenyl) sulfonyl]-3-(2,5-difluorophenyl)cyclobutyl]-1,1,1-trifluoromethanesulfonamide (described in US20110263580); 1,1,1-trifluoro-N-(4-[5-fluoro-2-(trifluoromethyl)phenyl]-4-{[4-(trifluoromethyl)phenyl]sulfonyl}cyclohexyl) methanesulfonamide (described in US20110263580); gamma-Secretase Inhibitor I (also known as Z-Leu-Leu-Nle-CHO, benzyloxycarbonyl-leucyl-leucyl-norleucinal, available from Calbiochem); gamma-secretase inhibitor II:

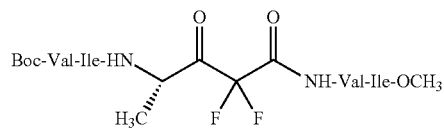

(MOL)(CDX) (available from Calbiochem); gamma secretase inhibitor III, (N-Benzyloxycarbonyl-Leu-leucinal, available from Calbiochem); gamma secretase inhibitor IV, (N-(2-Naphthoyl)-Val-phenylalaninal, available from Calbiochem); gamma-secretase inhibitor V (also known as Z-LF-CHO, N-Benzyloxycarbonyl-Leu-phenylalaninal, available from EMD Millipore); gamma-secretase inhibitor VI (1-(S)-endo-N-(1,3,3)-Trimethylbicyclo[2.2.1]hept-2-yl)-4-fluorophenyl Sulfonamide, available from EMD Millipore); gamma secretase inhibitor VII, (also known as Compound A, MOC-LL-CHO, Menthyloxycarbonyl-LL-CHO, available from Calbiochem); gamma secretase inhibitor X, ({1S-Benzyl-4R-[1-(1S-carbamoyl-2-phenethylcarbamoyl)-1S-3-methylbutylcarbamoyl]-2R-hydroxy-5-phenylpentyl}carbamic acid tert-butyl ester, available from Calbiochem); gamma secretase inhibitor XI, (7-Amino-4-chloro-3-methoxyisocoumarin, available from Calbiochem); gamma secretase inhibitor XII, (also known as Z-Ile-Leu-CHO, Shih and Wang, Cancer Res. 67: 1879-1882, 2007); gamma secretase inhibitor XIII, (Z-Tyr-Ile-Leu-CHO, available from Calbiochem); gamma secretase inhibitor XIV, (Z-Cys(t-Bu)-Ile-Leu-CHO, available from Calbiochem); gamma secretase inhibitor XVII, (also known as WPE-III-31C),

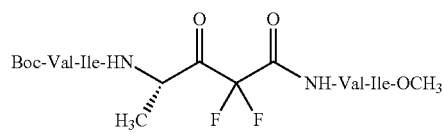

(MOL)(CDX) (available from Calbiochem); gamma secretase inhibitor XIX, (also known as benzodiazepine, (2S,3R)-3-(3,4-Difluorophenyl)-2-(4-fluorophenyl)-4-hydroxy-N-((3 S)-2-oxo-5-phenyl-2,3-dihydro-1H-benzo[e][1,4]diazepin-3-yl)-butyramide, Churcher et al., J Med Chem. 46(12):2275-8, 2003); gamma secretase inhibitor XX, (also known as dibenzazepine, (S,S)-2-[2-(3,5-Difluorophenyl)acetylamino]-N-(5-methyl-6-oxo-6,7-dihydro-5H-dibenzo[b,d]azepin-7-yl)propionamide,

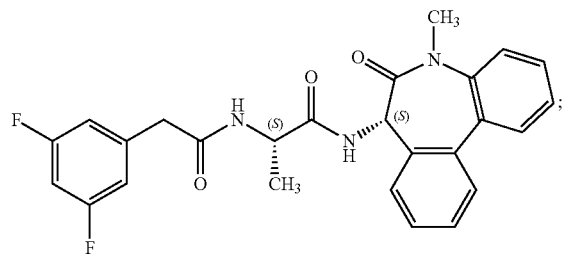

(MOL)(CDX) (Weihofen et al., Science 296: 2215-2218, 2002, available from Calbiochem); gamma secretase inhibitor XXI, ((S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide, available from Calbiochem); 5-methyl-2-propan-2-ylcyclohexyl)N-[4-methyl-1-[(4-methyl-1-oxopentan-2-yl)amino]-1-oxopentan-2-yl]carbamate (available from HDH Pharma Inc.); N-trans-3,5-Dimethoxycinnamoyl-Ile-leucinal (available from Calbiochem); N-tert-Butyloxycarbonyl-Gly-Val-Valinal; isovaleryl-V V-Sta-A-Sta-OCH3 (available from Calbiochem); diethyl-(5-phenyl-3H-azepin-2-yl)-amine (described in U.S. Pat. No. 8,188,069); diethyl-(5-isopropyl-3H-azepin-2-yl)-amine (described in U.S. Pat. No. 8,188,069); diethyl-(4-phenyl-3H-azepin-2-yl)-amine (described in U.S. Pat. No. 8,188,069); diethyl-(6-phenyl-3H-azepin-2-yl)-amine (described in U.S. Pat. No. 8,188,069); 5-phenyl-1,3-dihydro-azepin-2-one (described in U.S. Pat. No. 8,188,069); 5-Isopropyl-1,3-dihydro-azepin-2-one (described in U.S. Pat. No. 8,188,069); 4-phenyl-1,3-dihydro-azepin-2-one (described in U.S. Pat. No. 8,188,069); 6-phenyl-1,3-dihydro-azepin-2-one (described in U.S. Pat. No. 8,188,069); 2-butoxy-5-phenyl-3H-azepine (described in U.S. Pat. No. 8,188,069); 1-methyl-5-phenyl-1,3-dihydro-azepin-2-one (described in U.S. Pat. No. 8,188,069); 5-isopropyl-1-methyl-1,3-dihydro-azepin-2-one (described in U.S. Pat. No. 8,188,069); 1-methyl-4-phenyl-1,3-dihydro-azepin-2-one (described in U.S. Pat. No. 8,188,069); 1-methyl-6-phenyl-1,3-dihydro-azepin-2-one (described in U.S. Pat. No. 8,188,069); 1-methyl-5-phenyl-1H-azepine-2,3-dione-3-oxime (described in U.S. Pat. No. 8,188,069); 5-isopropyl-1-methyl-1H-azepine-2,3-dione-3-oxime (described in U.S. Pat. No. 8,188,069); 1-methyl-6-phenyl-1H-azepine-2,3-dione-3-oxime (described in U.S. Pat. No. 8,188,069); 1-methyl-4-phenyl-1H-azepine-2,3-dione-3-oxime (described in U.S. Pat. No. 8,188,069); 3-amino-1-methyl-5-phenyl-1,3-dihydro-azepin-2-one (described in U.S. Pat. No. 8,188,069); 3-amino-5-isopropyl-1-methyl-1,3-dihydro-azepin-2-one (described in U.S. Pat. No. 8,188,069); 3-amino-1-methyl-4-phenyl-1,3-dihydro-azepin-2-one (described in U.S. Pat. No. 8,188,069); 3-amino-1-methyl-6-phenyl-1,3-dihydro-azepin-2-one (described in U.S. Pat. No. 8,188,069); (S)-[1-(1-methyl-2-oxo-5-phenyl-2,3-dihydro-1H-azepin-3-ylcarbamoyl)-ethyl]-carbamic acid tertbutyl ester (described in U.S. Pat. No. 8,188,069); [(S)-1-(5-isopropyl-1-methyl-2-oxo-2,3-dihydro-1H-azepin-3-ylcarbamoyl)-ethyl]carbamic acid tert-butyl ester (described in U.S. Pat. No. 8,188,069); [(S)-1-(1-methyl-2-oxo-4-phenyl-2,3-dihydro-1H-azepin-3-ylcarbamoyl)-ethyl] carbamic acid tert-butyl ester (described in U.S. Pat. No. 8,188,069); [(S)-1-(1-methyl-2-oxo-6-phenyl-2,3-dihydro-1H-azepin-3-ylcarbamoyl)-ethyl]-carbamic acid tert-butyl ester (described in U.S. Pat. No. 8,188,069); (S)-2-amino-N-(1-methyl-2-oxo-5-phenyl-2,3-dihydro-1H-azepin-3-yl)-propionamide (described in U.S. Pat. No. 8,188,069); (S)-2-amino-N-(5-isopropyl-1-methyl-2-oxo-2,3-dihydro-1H-azepin-3-yl)propionamide (described in U.S. Pat. No. 8,188,069); (S)-2-Amino-N-(l-methyl-2-oxo-6-phenyl-2,3-dihydro-1H-azepin-3-yl)propionamide hydrochloride (described in U.S. Pat. No. 8,188,069); (S)-2-Amino-N-(l-methyl-2-oxo-4-phenyl-2,3-dihydro-1H-azepin-3-yl)propionamide hydrochloride (described in U.S. Pat. No. 8,188,069); (S)-2-fluoro-3-methyl-butyric acid (described in U.S. Pat. No. 8,188,069); (S)-2-hydroxy-3-methyl-N—[(S)-1-((S)-1-methyl-2-oxo-5-phenyl-2,3-dihydro-1H-azepin-3-ylcarbamoyl)-ethyl]-butyramide (described in U.S. Pat. No. 8,188,069); (S)-2-fluoro-3-methyl-N—[(S)-1-(1-methyl-2-oxo-5-phenyl-2,3-dihydro-1H-azepin-3-ylcarbamoyl)-ethyl]-butyramide (described in U.S. Pat. No. 8,188,069); (S)-2-hydroxy-N—[(S)-1-(5-isopropyl-1-methyl-2-oxo-2,3-dihydro-1H-azepin-3-ylcarbamoyl)ethyl]-3-methyl-butyramide (described in U.S. Pat. No. 8,188,069); (S)-2-hydroxy-3-methyl-N—[(S)-1-(1-methyl-2-oxo-4-phenyl-2,3-dihydro-1H-azepin-3-ylcarbamoyl)-ethyl]-butyramide (described in U.S. Pat. No. 8,188,069); (S)-2-hydroxy-3-methyl-N—[(S)-1-(1-methyl-2-oxo-6-phenyl-2,3-dihydro-1H-azepin-3-ylcarbamoyl)-ethyl]-butyramide (described in U.S. Pat. No. 8,188,069); and(S)-2-fluoro-3-methyl-N—[(S)-1-(1-methyl-2-oxo-6-phenyl-2,3-dihydro-1H-azepin-3-ylcarbamoyl)-ethyl]-butyramide (described in U.S. Pat. No. 8,188,069), or pharmaceutically acceptable salts thereof.

Additional examples of gamma-secretase inhibitors are disclosed in U.S. Patent Application Publication Nos. 2004/0029862, 2004/0049038, 2004/0186147, 2005/0215602, 2005/0182111, 2005/0182109, 2005/0143369, 2005/0119293, 2007/0190046, 2008/008316, 2010/0197660 and 2011/0020232; U.S. Pat. Nos. 6,756,511; 6,890,956; 6,984,626; 7,049,296; 7,101,895; 7,138,400; 7,144,910; 7,183,303; 8,188,069; and International Publication Nos. WO 1998/28268; WO 2001/70677, WO 2002/049038, WO 2004/186147, WO 2003/093253, WO 2003/093251, WO 2003/093252, WO 2003/093264, WO 2005/030731, WO 2005/014553, WO 2004/039800, WO 2004/039370, WO 2009/023453, EP 1720909, EP 2178844, EP 2244713.

The entire disclosures of all of the foregoing are hereby incorporated by reference herein.

Atoh1 Stimulatory Compounds

Compounds that promote progenitor cell differentiation to Atoh1+ hair cells include one or more of CHIR99021, LY411575, vorinostat, MEEI-0000489, MEEI-0087336, MEEI-0007991, 1-Azakenpaullone, BIO, WAY-262611, NP031112, MG-132, IM-12, Trichostatin A, HLY78, and PF03084014. In some embodiments, a combination of CHIR99021 and LY411575 is used.

GSK-3-Beta Inhibitors

GSK3β inhibitors include, but are not limited to, lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl)urea (AR-A014418), and indirubins (e.g., indirubin-5-sulfonamide; indirubin-5-sulfonic acid (2-hydroxyethyl)-amide indirubin-3'-monoxime;

5-iodo-indirubin-3'-monoxime; 5-fluoroindirubin; 5,5'-dibromoindirubin; 5-nitroindirubin; 5-chloroindirubin; 5-methylindirubin, 5-bromoindirubin), 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), and H-KEAPPAPPQSpP-NH2 (L803) or its cell-permeable derivative Myr-N-GKEAPPAPPQSpP-NH2 (L803-mts). Other GSK3β inhibitors are disclosed in U.S. Pat. Nos. 6,417,185; 6,489,344; 6,608,063 and Published U.S. Applications Nos. 690497, filed Oct. 20, 2003; 468605, filed Aug. 19, 2003; 646625, filed Aug. 21, 2003; 360535, filed Feb. 6, 2003; 447031, filed May 28, 2003; and 309535 filed Dec. 3, 2002. In some embodiments, the methods include administration of a CK1 inhibitor (e.g., a small molecule CK1 inhibitor) and a GSK3β inhibitor, plus one or both of a gamma-secretase inhibitor and/or an Atoh1 stimulatory compound as described herein.

Methods of Treatment

The combinations and methods described herein are appropriate for the treatment of mammalian (e.g., human) subjects who have or are at risk of developing hearing disorders resulting from cochlear hair cell loss. In some embodiments the subjects are post-neonatal (e.g., child, adolescent or adult, e.g., above the age of 1, 2, 3, 4, 5, 6, 7, 8, 9, 10, 11, 12 or 13 years) subjects. The methods described herein can be used to treat cochlear hair cell loss and any disorder that arises as a consequence of hair cell loss in the ear, such as hearing impairments or deafness. These subjects can receive treatment with a combination of agents as described herein. The approach may be optimal for treatment of acute hearing loss shortly after the damage has occurred, and may be less effective after longer time periods when Notch signaling has returned to its baseline level in the adult.

In some instances, methods include selecting a subject. Subjects suitable for treatment include those at risk of hair cell loss or with hair cell loss and/or those at risk of sensorineural hearing loss or with sensorineural hearing loss. Any subject experiencing or at risk for developing hearing loss is a candidate for the treatment methods described herein. A human subject having or at risk for developing a hearing loss can hear less well than the average human being, or less well than a human before experiencing the hearing loss. For example, hearing can be diminished by at least 5, 10, 30, 50% or more.

The subject can have hearing loss associated with cochlear hair cell loss for any reason, or as a result of any type of event. For example, a subject can be deaf or hard-of-hearing as a result of an infection or physical ototoxic insult, e.g., a traumatic event, such as a physical trauma to a structure of the ear that does not irreversibly damage the supporting cells. In preferred embodiments, the subject can have (or be at risk of developing) hearing loss as result of exposure to a sudden loud noise, or a prolonged exposure to loud noises. For example, prolonged or repeated exposures to concert venues, airport runways, and construction areas can cause inner ear damage and subsequent hearing loss; subjects who are subjected to high levels of environmental noise, e.g., in the home or workplace, can be treated using the methods described herein. A subject can have a hearing disorder that results from aging, e.g., presbycusis, which is generally associated with normal aging processes; see, e.g., Huang, Minn. Med. 90(10):48-50 (2007) and Frisina, Annals of the New York Academy of Sciences, 1170: 708-717 (2009), and can occur in subjects as young as 18, but is generally more marked in older subjects, e.g., subjects over age 40, 45, 50, 55, 60, 65, 70, 75, 80, 85, or 90. A subject can have tinnitus (characterized by ringing in the ears) due to loss of hair cells. A subject can experience a chemical ototoxic insult, wherein ototoxins include therapeutic drugs including antineoplastic agents, salicylates, quinines, and aminoglycoside antibiotics, e.g., as described further below, contaminants in foods or medicinals, and environmental or industrial pollutants. In general, subjects who have a known genetic disease associated with hearing loss (e.g., mutations in connexin 26, Alport, and so on), or a known cause of hearing loss that is associated with structural damage to the inner ear (e.g. penetrating trauma), that would not be correctable or ameliorated by the present methods are excluded from the present methods. In some embodiments, subjects who lack supporting cells, e.g., who have no LGR5+ cells in their cochlea, are excluded from treatment, or are administered LGR5+ cells as part of the treatment.

In some embodiments, the methods include administering to the subject a compound described herein within one, two, three, four, five, six, or seven days, or one, two, three, four, five, or six weeks of exposure to an ototoxic insult, e.g., a physical (noise, trauma) or chemical (ototoxin) insult that results in or could result in a loss of hair cells, and causes an increase in Notch signaling in the subject.

In some embodiments, a subject suitable for the treatment using the compounds and methods featured in the invention can include a subject having a vestibular dysfunction, including bilateral and unilateral vestibular dysfunction; the methods include administering a therapeutically effective amount of an agent described herein, e.g., by systemic administration or administration via the endolymphatic sac (ES). Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunctions that can be treated by the methods described herein can be the result of a genetic or congenital defect; an infection, such as a viral or bacterial infection; or an injury, such as a traumatic or nontraumatic injury, that results in a loss of vestibular hair cells. In some embodiments, balance disorders or Meniere's disease (idiopathic endolymphatic hydrops) may be treated by the methods described herein. Vestibular dysfunction is most commonly tested by measuring individual symptoms of the disorder (e.g., vertigo, nausea, and fuzzy vision).

Alternatively or in addition, the compounds and methods featured in the invention can be used prophylactically, such as to prevent, reduce or delay progression of hearing loss, deafness, or other auditory disorders associated with loss of hair cells. For example, a composition containing one or more compounds can be administered with (e.g., before, after or concurrently with) an ototoxic therapy, i.e., a therapeutic that has a risk of hair cell toxicity and thus a risk of causing a hearing disorder. Ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin;

diuretics; salicylates such as aspirin; and certain malaria treatments such as quinine and chloroquine. For example, a subject undergoing chemotherapy can be treated using the compounds and methods described herein. The chemotherapeutic agent cisplatin, for example, is known to cause hearing loss. Therefore, a composition containing one or more compounds can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

In general, the compounds and methods described herein can be used to generate hair cell growth in the ear and/or to increase the number of hair cells in the ear (e.g., in the inner, middle, and/or outer ear). For example, the number of hair cells in the ear can be increased about 2-, 3-, 4-, 6-, 8-, or 10-fold, or more, as compared to the number of hair cells before treatment. This new hair cell growth can effectively restore or establish at least a partial improvement in the subject's ability to hear. For example, administration of an agent can improve hearing loss by about 5, 10, 15, 20, 40, 60, 80, 100% or more.

In some instances, compositions can be administered to a subject, e.g., a subject identified as being in need of treatment, using a systemic route of administration. Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; transdermal routes of administration; and inhalation (e.g., nasal sprays).

In some instances, compositions can be administered to a subject, e.g., a subject identified as being in need of treatment, using a systemic or local route of administration. Such local routes of administration include administering one or more compounds into the ear of a subject and/or the inner ear of a subject, for example, by injection and/or using a pump.

In some instances, compositions can be can be injected into the ear (e.g., auricular administration), such as into the luminae of the cochlea (e.g., the Scala media, Sc vestibulae, and Sc tympani). For example, compositions can be administered by intratympanic injection (e.g., into the middle ear), intralabyrinthine delivery (e.g., to the stapes foot plate), and/or injections into the outer, middle, and/or inner ear. Such methods are routinely used in the art, for example, for the administration of steroids and antibiotics into human ears. Injection can be, for example, through the round window of the ear or through the cochlea capsule. In another exemplary mode of administration, compositions can be administered in situ, via a catheter or pump. A catheter or pump can, for example, direct a pharmaceutical composition into the cochlea luminae or the round window of the ear. Exemplary drug delivery apparatus and methods suitable for administering one or more compounds into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a subject during a surgical procedure. In some embodiments, a catheter or pump can be positioned, e.g., in the ear (e.g., the outer, middle, and/or inner ear) of a subject without the need for a surgical procedure.

In some instances, compositions can be administered in combination with a mechanical device such as a cochlea implant or a hearing aid, which is worn in the outer ear. An exemplary cochlea implant that is suitable for use with the present invention is described by Edge et al., (U.S. Publication No. 2007/0093878).

In some instances, compositions can be administered according to any of the Food and Drug Administration approved methods, for example, as described in CDER Data Standards Manual, version number 004 (which is available at fda.give/cder/dsm/DRG/drg00301.htm).

In some instances, the present disclosure includes treating a subject by administering to the subject cells produced using the compositions and methods disclosed herein. In general, such methods can be used to promote complete or partial differentiation of a cell to or towards a mature cell type of the inner ear (e.g., a hair cell) in vitro. Cells resulting from such methods can then be transplanted or implanted into a subject in need of such treatment. Cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described herein. Target cells suitable for use in these methods are described above.

In some instances, methods can include administering one or more compositions disclosed herein and cells produced using the compositions and methods disclosed herein to a subject.

Administration of cells to a subject, whether alone or in combination with compounds or compositions disclosed herein, can include administration of undifferentiated, partially differentiated, and fully differentiated cells, including mixtures of undifferentiated, partially differentiated, and fully differentiated cells. As disclosed herein, less than fully differentiated cells can continue to differentiate into fully differentiated cells following administration to the subject.

Where appropriate, following treatment, the subject can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a subject can hear. Hearing tests in humans include behavioral observation audiometry (for infants to seven months), visual reinforcement orientation audiometry (for children 7 months to 3 years); play audiometry for children older than 3 years; and standard audiometric tests for older children and adults, e.g., whispered speech, pure tone audiometry; tuning fork tests; brain stem auditory evoked response (BAER) testing or auditory brain stem evoked potential (ABEP) testing. Oto-acoustic emission testing can be used to test the functioning of the cochlear hair cells, and electro-cochleography provides information about the functioning of the cochlea and the first part of the nerve pathway to the brain. In some embodiments, treatment can be continued with or without modification or can be stopped.

EXAMPLES

The invention is further described in the following examples, which do not limit the scope of the invention described in the claims.

Example 1. CK1 Destabilizes Atoh1

We performed immunoprecipitation mass spectrometry (IP-MS) to identify binding partners of Atoh1 using a stably expressing 293T cell line prepared by lentiviral infection of pHAGE-FLAG-HA-Atoh1[1]. Lysates of FLAG-HA-Atoh1 293T cells immunoprecipitated with HA antibody were subjected to mass spectrometry Two isoforms of casein kinase, CK1δ and ε were found associated with Atoh1 (Table I).

Figure 1:
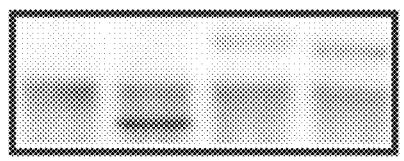
FIG. 1. CK1 binds to Atonal homolog 1 (Atoh1) and decreases steady-state Atoh1 level HEK cells were co-transfected with FLAG Atoh1 plasmid and HA-CK1 plasmids (including CK1α, CK1δ, and CK1ε). Immunoprecipitation was performed under denaturing conditions with an anti-FLAG antibody. Ck1 was detected with an anti-Myc antibody while Atoh1 was detected with anti-FLAG antibody.
Figure 1:

Atoh1-CK1 association was further validated by co-immunoprecipitation confirming that CK1 binds to Atoh1 (FIG. 1). We also found that CK1 overexpression decreased steady-state level of Atoh1.

Figure 2:
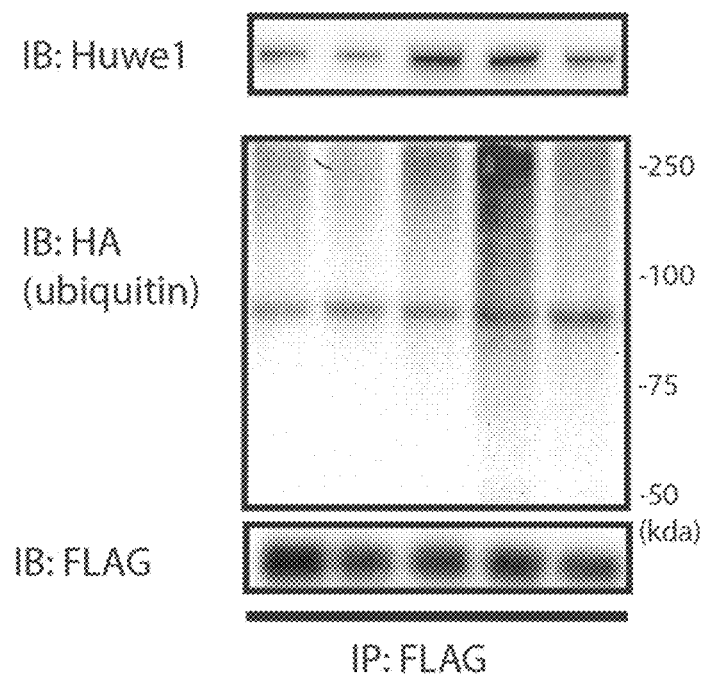
FIG. 2. CK1 inhibitor diminishes Huwe1 binding and decreases ubiquitylation of Atoh1

We previously found that Huwe1, an E3 ubiquitin ligase, directed Atoh1 degradation to the proteasome (see Cheng, "Role of the ubiquitin-proteasome pathway in the inner ear: identification of an E3 ubiquitin ligase for Atoh1," Thesis: Ph. D., Harvard-MIT Program in Health Sciences and Technology, 2014, available online at hdl.handle.net/1721.1/96458; and PCT/US2015/043976). To explore the effect of CK1 on proteasomal degradation of Atoh1, we performed co-IP experiments. We found that two small molecule CK1 inhibitors, D4476 and PF-670462, diminished Atoh1-Huwe1 binding and subsequent ubiquitylation (FIG. 2).

TABLE I

Mass spectrometric analysis to confirm immunoprecipitation of Atoh1 and CK1

| Gene symbol | Total peptide | Unique peptide | Average peptide score | Protein coverage |
|---|---|---|---|---|
| TUBB2A | 159 | 40 | 3.0903 | 55.51% |
| ATOH1 | 155 | 19 | 2.1144 | 34.18% |
| TUBA1A | 112 | 34 | 3.1383 | 66.08% |
| RPL4 | 106 | 36 | 2.4767 | 53.63% |
| EEF1A1 | 103 | 28 | 2.6454 | 58.87% |
| TUFM | 72 | 38 | 3.2781 | 68.36% |
| RPL3 | 67 | 29 | 2.5399 | 45.66% |
| SSB | 65 | 30 | 2.8608 | 5.43% |
| RBMX | 65 | 27 | 2.5009 | 47.06% |
| ENO1 | 62 | 34 | 3.1674 | 58.29% |
| PSMC5 | 52 | 31 | 3.5295 | 64.29% |
| PSMC2 | 50 | 29 | 2.9925 | 63.74% |
| YARS2 | 11 | 8 | 3.3677 | 29.77% |
| TUBA1C | 7 | 11 | 3.6062 | 15.14% |
| SERPINH1 | 9 | 7 | 2.5123 | 20.81% |
| CSNK1D | 7 | 4 | 3.1615 | 12.5% |
| CSNK1E | 6 | 3 | 2.8233 | 9.86% |
| ACOX1 | 5 | 4 | 2.8799 | 10.30% |
| BCKDHA | 5 | 3 | 2.6629 | 9.44% |
| PRPS1 | 3 | 3 | 2.6642 | 18.46% |
| TUBB2B | 2 | 1 | 3.0318 | 2.70% |
| TUBA4A | 1 | 1 | 3.4258 | 31.31% |
| PRDX4 | 1 | 1 | 3.1432 | 7.01% |
| AAMP | 1 | 1 | 2.3377 | 2.53% |
| PDE4B | 1 | 1 | 2.2331 | 2.04% |

Coomassie blue stained bands were excised and subjected to mass spectrometric analysis after immunoprecipitation of Atoh1 and its associated binding partners.

Example 2. Evolutionarily Conserved Serines in the C-Terminus Account for Atoh1 Stability We generated a panel of deletions of Atoh1, retaining the bHLH domain (FIG. 3A, right panel). Of two N-terminal (Δ10-93 for deletion 1 and Δ94-156 for deletion 2) and two C-terminal (Δ214-305 for deletion 3 and Δ306-347 deletion 4) deletions, Atoh1-deletion 4 had the longest half-life based on a cycloheximide chase assay, suggesting that motifs affecting the half-life of Atoh1 fell between amino acids 306 and 347 (FIGS. 3A-B).

Deletion in the serine-enriched C-terminal motif diminished Huwe1 binding and subsequent ubiquitylation, indicating that sequences affecting involved in E3 ubiquitin ligase binding and enzymatic activity toward Atoh1 may lie in this area (FIG. 4).

Cross-species sequence comparison of Atoh1 by MegaAlign (DNAstar, Madison, WI) indicated that serines 309, 325, 328, 331 and 334 were conserved across species (FIG. 5A). Since conservation may relate to biological function, we generated mutated Atoh1 plasmids containing alanine in the place of each serine. The S334A mutant was protected from degradation based on its higher level of expression and the lack of any further effect of proteasome inhibition with MG132, while other mutants were affected to a similar extent as wild-type Atoh1 (FIG. 5B). Mutations at positions 328 and 331 had modest effects, while mutation at position 334 dramatically prolonged the half-life of Atoh1 (FIG. 5C). Co-immunoprecipitation also showed that S334 mutation affected Huwe1 binding and ubiquitylation (FIG. 6). We conclude that Ser 334 in the C-terminus of Atoh1 contains a motif ("degron") that specifies Atoh1 for proteasomal degradation.

Example 3. Mass Spectrometry Identifies Atoh1 Phosphorylation in the Presence of CK1 Overexpression Atoh1 phosphorylation sites controlled by CK1, Mass spectrometry analysis of immunoprecipitated Atoh1 from FLAG-Atoh1 plasmids in HEK cells with or without CK1 showed that, among the conserved serine sites on the C-terminus of Atoh1, Serine 325, 328 and 334 were phosphorylated after CK1 overexpression (Table II). These data indicate that Atoh1 phosphorylation at S334 is critical for CK1-mediated Atoh1 degradation.

TABLE II

Summary of Atoh1 Phosphorylation

| Position[a] | Atoh1[b] | Atoh1 + CK1[c] | Conservation[d] | Contribution to stability[e] | Peptide[f] | SEQ ID NO: |
|---|---|---|---|---|---|---|
| 82 | x | x | Y | N/A | AAQYLLHSPELGASEAAAPR | 1 |
| 99 | x | x | N | N/A | DEADSQGELVR | 2 |
| 309 | x | x | N | No | DLSPSLPGGILQPVQEDNSK | 3 |
| 311 |  | x | N** | N/A | DLSPSLPGGILQPVQEDNSK | 4 |
| 325 |  | x | Y | No | DLSPSLPGGILQPVQEDNSKTSPR | 5 |

TABLE II-continued

Summary of Atoh1 Phosphorylation

| Position[a] | Atoh1[b] | Atoh1 + CK1[c] | Conservation[d] | Contribution to stability[e] | Peptide[f] | SEQ ID NO: |
|---|---|---|---|---|---|---|
| 328 |  | x | Y | Low | DLSPSLPGGILQPVQEDNSKTSPR | 6 |
| 331 | x |  | Y | Low | SHRSDGEFSPHSHYSDSDEAS | 7 |
| 334 |  | x | Y | High | SDGEFSPHSHYSDSDEAS | 8 |
| 339 | x |  | N* | N/A | SDGEFS#PHSHYSDSDEAS | 9 |
| 345 | X |  | N* | N/A | SDGEFSPHSHYSDSDEAS | 10 |
| 347 | X |  | N* | N/A | SDGEFSPHSHYSDSDEAS | 11 |

[a]Position of the amino acids
[b]Atoh1 overexpression only
[c]Atoh1 and CK1 overexpression
[d]Cross-species sequence comparison. Y: conserved, N*: non-conserved in one tested species, N**: non-conserved in two tested species, N: non-conserved
[e]Cycloheximide-chase assay results shown in FIG. 5
[f]Phosphorylated peptide sequence: phosphorylation is underlined

Example 4. CK1 Regulates Downstream Signaling by Atoh1

To further assess potential roles of CK1 in the control of Atoh1 signaling, we performed dual luciferase reporter assays using a firefly reporter construct with an Atoh1 E-box associated motif (AtEAM) and a *Renilla* control reporter. AtEAM is a ten amino acid Atoh1-specific binding motif that represents the site for the activity of Atoh1 in numerous downstream genes (Klisch et al., Proc Natl Acad Sci USA. 2011 Feb. 22; 108(8):3288-93). Inhibition of CK1 by D4476 increased and overexpression of CK1 (specifically CK1δ and/or CK1ε) reduced Atoh1 downstream signaling (FIG. 7A).

We then compared the effects on E-box luciferase activity of wild-type Atoh1 vs the serine mutants at the conserved Atoh1 C-terminus after overexpression of CK1δ and CK1ε (FIG. 7B). CK1 overexpression caused a significant decrease in downstream signaling in S325A, S328A, S331A and S339A, but not wild-type or S334A Atoh1 (FIG. 7C), supporting a role of CK1 mediated S334 phosphorylation in cellular Atoh1 activity.

Example 5. CK1 Inhibition Increased Hair Cell Generation in the Organ of Corti Treatment of organ of Corti explants from newborn mice with 10 μM CK1 inhibitor D4476 for 72 hours caused stabilization of Atoh1 protein in the cochlea based on densitometry (FIG. 8).

Since CK1 inhibition stabilized Atoh1, we assessed its effect on hair cell generation in the cochlea. A Sox2-positive Cre-reporter strain crossed with CAG-TdTomato (Bramhall et al., Stem cell reports 2, 311-322 (2014)) was used to label all supporting cells for lineage tracing to follow supporting cells after CK1 inhibition. Treatment of organ of Corti explants with 10 μM CK1 inhibitor D4476 for 72 hours significantly increased the number of reporter-labeled outer and inner hair cells in all regions of cochlea (FIG. 9), indicating that the hair cells made after CK1 inhibition came from Sox2-positive supporting cells.

Example 6. CK1 Inhibition Promoted Hair Cell Regeneration after Aminoglycoside Damage Aminoglycoside-exposed organ of Corti explants[3] were treated with 10 μM D4476 for 72 hours and lineage traced. The treatment resulted in an increase of Sox2-lineage-tagged hair cells (cells co-labeled with myosin VIIa and TdTomato) indicating that Atoh1 stabilization by CK1 inhibition regenerated hair cells (FIG. 10).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has or is at risk of developing hearing loss or vestibular dysfunction, the method comprising:
   identifying a subject who has experienced, or is at risk for developing, hearing loss or vestibular dysfunction; and
   administering to the subject one or more nucleic acids that target casein kinase 1 (CK1) epsilon and/or CK1 delta, and one or more compounds that stimulate Atoh1 gene expression.

2. The method of claim 1, wherein the subject has or is at risk for developing sensorineural hearing loss, auditory neuropathy, or both.

3. The method of claim 1, wherein the subject has or is at risk for developing a vestibular dysfunction that results in dizziness, imbalance, or vertigo.

4. The method of claim 1, wherein the one or more inhibitory nucleic acids that target CK1 epsilon and/or CK1 delta, and/or the one or more compounds that stimulate Atoh1 gene expression is administered systemically.

5. The method of claim 1, wherein the one or more inhibitory nucleic acids that target CK1 epsilon and/or CK1 delta, and/or the one or more compounds that stimulate Atoh1 gene expression is administered locally to the inner ear.

6. The method of claim 1, wherein the one or more inhibitory nucleic acids that target CK1 epsilon and/or CK1 delta is shRNA or siRNA.

7. The method of claim 1, wherein the method comprises administering to the subject one or more inhibitory nucleic acids that target CK1 epsilon.

8. The method of claim 1, wherein the method comprises administering to the subject one or more inhibitory nucleic acids that target CK1 delta.

9. The method of claim 1, wherein the one or more compounds that stimulate Atoh1 gene expression comprises a glycogen synthase kinase 3 beta (GSK-3-beta) inhibitor.

10. The method of claim 1, wherein the one or more compounds that stimulate Atoh1 gene expression comprises a gamma secretase inhibitor.

11. The method of claim 1, wherein the hearing loss or vestibular dysfunction is caused by aging.

12. The method of claim 1, wherein the hearing loss or vestibular dysfunction is caused by a genetic or congenital defect.

13. The method of claim 1, wherein the hearing loss or vestibular dysfunction is caused by noise or trauma.

14. The method of claim 1, wherein the hearing loss or vestibular dysfunction is caused by a chemical ototoxic insult.

* * * * *